(12) United States Patent
Tsuji

(10) Patent No.: US 12,256,941 B2
(45) Date of Patent: Mar. 25, 2025

(54) ENDOSCOPE CLIP

(71) Applicant: OLYMPUS CORPORATION, Hachioji (JP)

(72) Inventor: Tomohiro Tsuji, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 937 days.

(21) Appl. No.: 17/235,687

(22) Filed: Apr. 20, 2021

(65) Prior Publication Data

US 2021/0236134 A1 Aug. 5, 2021

Related U.S. Application Data

(63) Continuation of application No. PCT/JP2018/039152, filed on Oct. 22, 2018.

(51) Int. Cl.
*A61B 17/122* (2006.01)
*A61B 17/128* (2006.01)
*A61B 17/00* (2006.01)

(52) U.S. Cl.
CPC ...... *A61B 17/1285* (2013.01); *A61B 17/1227* (2013.01)

(58) Field of Classification Search
CPC ..... A61B 17/083; A61B 17/10; A61B 17/122; A61B 17/1227; A61B 17/128; A61B 17/1285; A61B 2017/00407; A61B 2017/0488; A61B 2017/2931
See application file for complete search history.

(56) References Cited

U.S. PATENT DOCUMENTS

2018/0078262 A1* 3/2018 Lehtinen .............. A61B 17/083
2018/0140300 A1* 5/2018 Randhawa ......... A61B 17/1227

FOREIGN PATENT DOCUMENTS

| CN | 104902827 A | 9/2015 |
|---|---|---|
| CN | 107405046 A | 11/2017 |
| EP | 2995263 A1 | 3/2016 |
| JP | 2013-085859 A | 5/2013 |
| JP | 2013-085860 A | 5/2013 |

(Continued)

OTHER PUBLICATIONS

Oct. 17, 2023 Office Action issued in Chinese Patent Application No. 202111588581.1.

(Continued)

*Primary Examiner* — Phong Son H Dang
*Assistant Examiner* — Lindsey R. Rivers
(74) *Attorney, Agent, or Firm* — Oliff PLC

(57) ABSTRACT

An endoscope clip has a clip unit having an arm member configured from a plurality of arms; an operation wire connected to the arm member and configured to move toward a distal end side to cause the arm member to transition from a closed configuration to an open configuration; and a restrictor, wherein the clip unit applies a biasing force to the operation wire toward the distal end side when the arm member is in the closed configuration, and when the arm member is in the closed configuration, the restrictor is configured to restrict the arm member from transitioning from the closed configuration to the open configuration by applying a force being opposite to the biasing force to the operation wire to restrict the movement of the operation wire toward the distal end side.

20 Claims, 29 Drawing Sheets

(56) References Cited

FOREIGN PATENT DOCUMENTS

| JP | 5750620 B2 | 7/2015 | | |
|---|---|---|---|---|
| WO | 2014/181678 A1 | 11/2014 | | |
| WO | WO-2014181676 A1 * | 11/2014 | ........... | A61B 17/122 |
| WO | WO-2018173474 A1 * | 9/2018 | ......... | A61B 17/1227 |

OTHER PUBLICATIONS

Jul. 5, 2022 Office Action issued in Japanese Patent Application No. 2020-551719.
Dec. 11, 2018 Search Report issued in International Patent Application No. PCT/JP2018/039152.

* cited by examiner

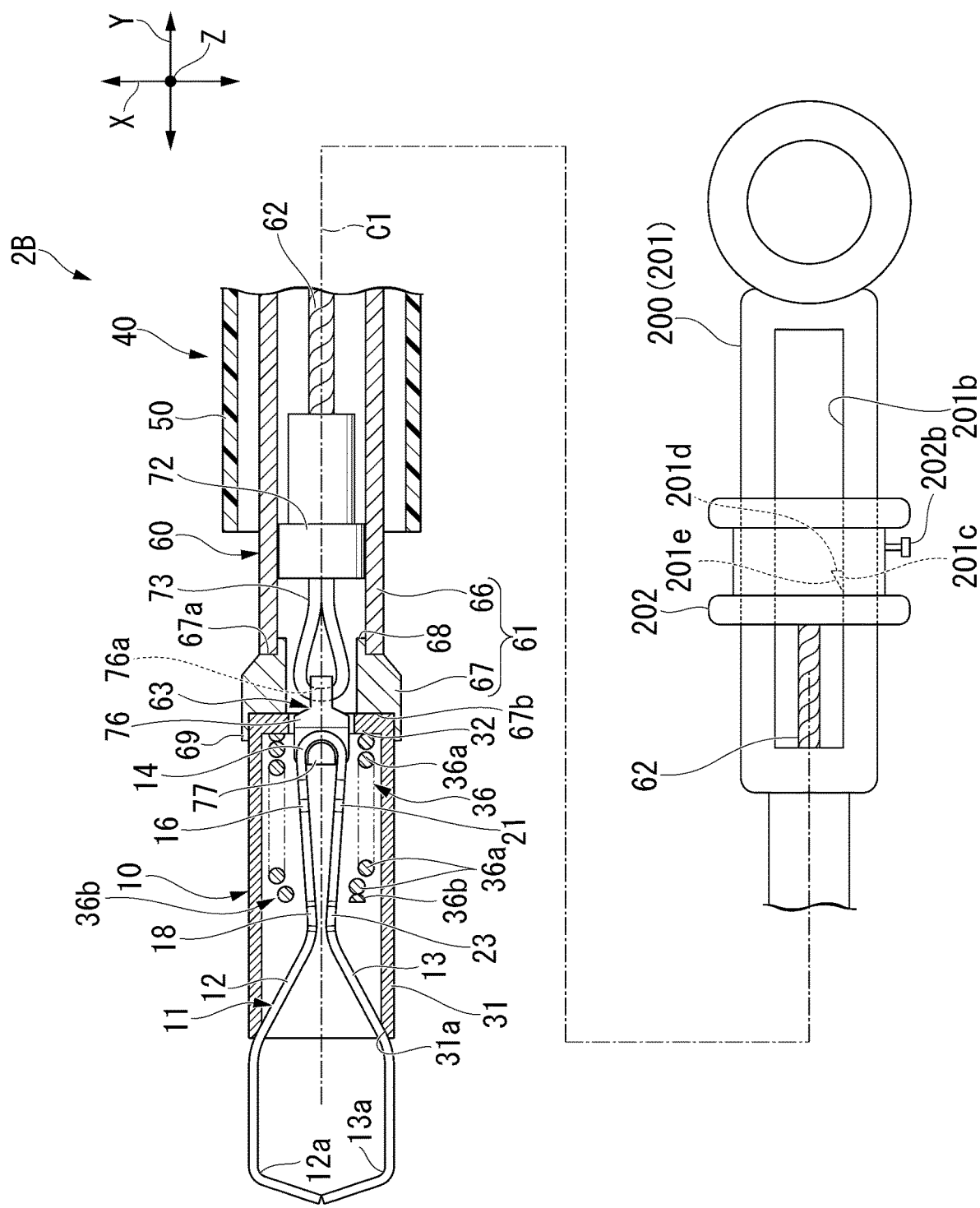

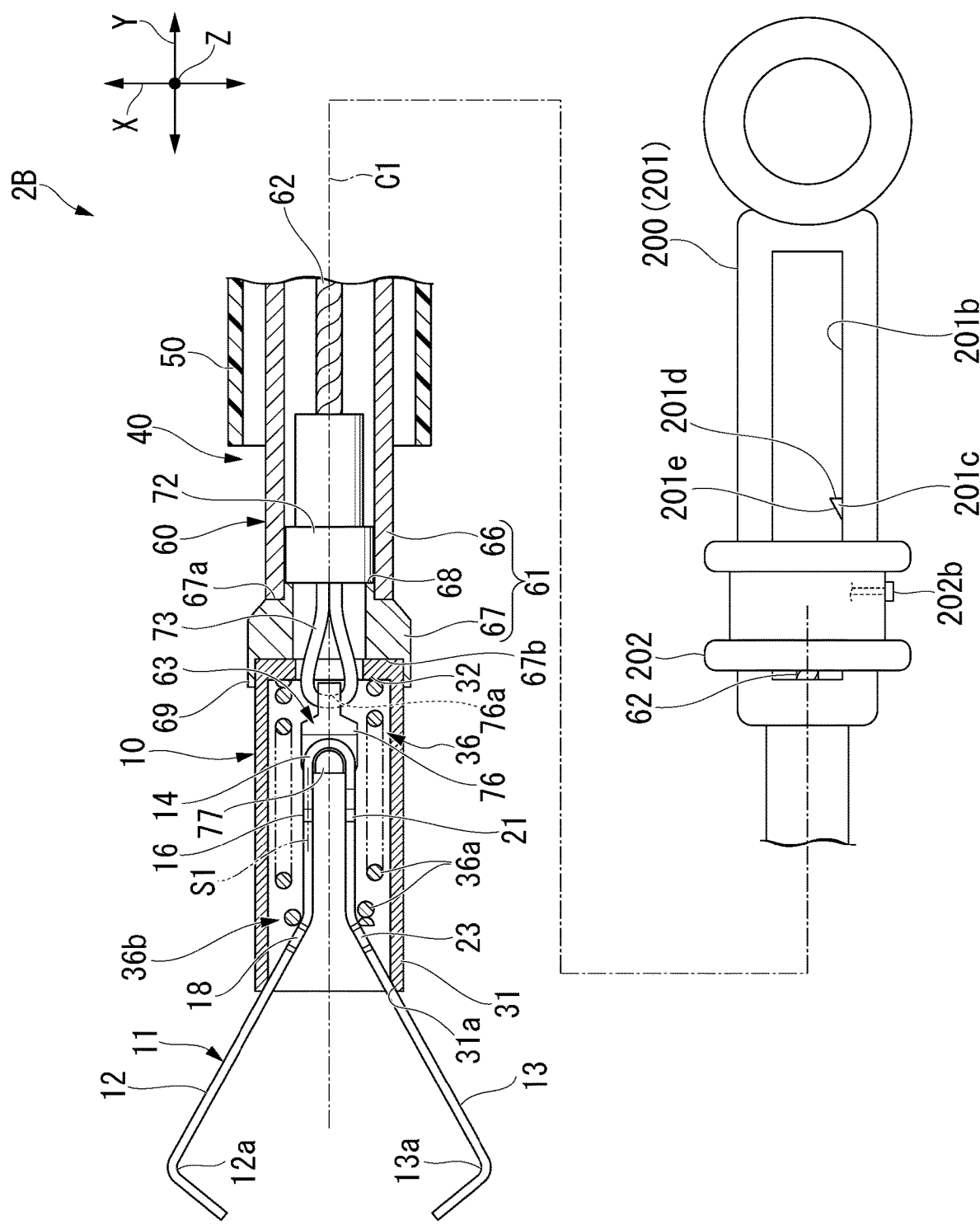

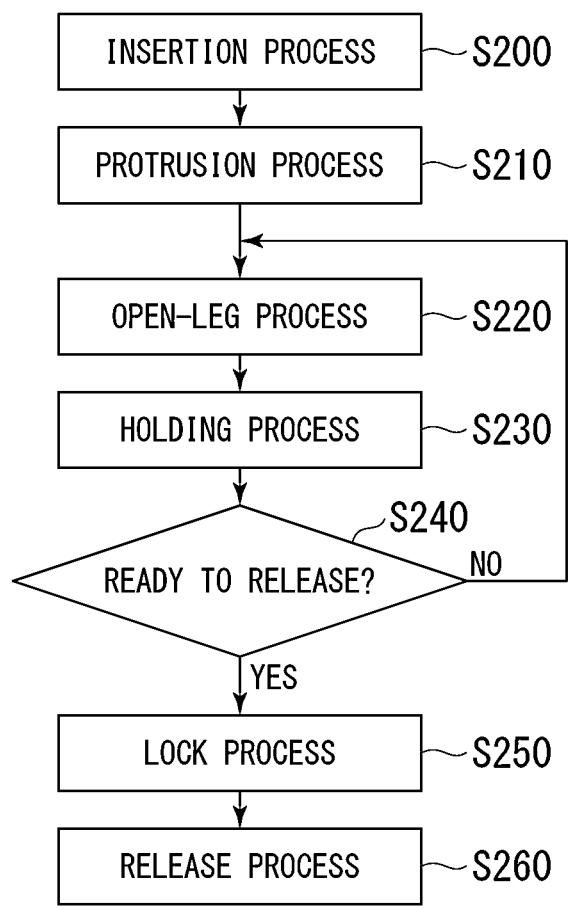

ENDOSCOPE CLIP

This application is a continuation application of PCT International Application No. PCT/JP2018/039152, filed on Oct. 22, 2018. The content of the PCT International Application is incorporated herein by reference.

TECHNICAL FIELD

The present disclosure relates to an endoscope clip configured for ligating tissues.

BACKGROUND ART

Conventionally known is an endoscope clip which is introduced into the body of a patient via a channel of an endoscope for a usage of ligating the openings and blood vessels formed in the tissue. An endoscopic treatment tool as described in Japanese Patent (Granted) No. 5750620 is known as such endoscope clip.

The endoscope treatment tool described in Japanese Patent (Granted) No. 5750620 includes a clip unit and a treatment tool body.

The clip unit has a clip main body, a pressing tube, and a spiral spring. The clip main body has a first arm and a second arm. The first arm and the second arm are separated from each other with a space between a distal end of the first arm and a distal end of the second arm when there is no external force applied thereto.

The treatment instrument body has an outer tube, an insertion portion, and an operating member. The insertion portion is inserted through the outer tube so as to be advanceable and retractable, and the insertion portion has a sheath, an operation wire, and a connection member. The operation wire is inserted into the sheath, wherein a distal end thereof is connected to the connection member, and a proximal end thereof is connected to a slider described below. The connection member is provided to connect the clip main body and the operation wire. The operating member is attached to a proximal end side of the insertion portion, and the operating member has an operating portion main body, a slider, and a breaking mechanism. The slider is configured to be advanceable and retractable with respect to the operating portion main body by engaging with a slit of the operating portion main body. The breaking mechanism is built in the operating member. When a tension applying to the breaking mechanism reaches or exceeds a predetermined tensile strength, the breaking mechanism is broken.

The endoscope treatment tool disclosed in Japanese Patent (Granted) No. 5750620 is used as follows.

An operator inserts the endoscope having the channel into the body of the patient. Next, the operator inserts the outer tube from the proximal end portion of the channel of the endoscope and projects the outer tube from the distal end portion of the channel of the endoscope. Subsequently, the operator pulls the outer tube back with respect to the insertion portion of the treatment tool main body to cause the clip main body to project from the distal end side of the outer tube. As a result, the first arm and the second arm of the clip main body enter an open configuration in which there is a gap generated between the first arm and the second arm.

When the operator directs the clip unit toward the target tissue inside the body of the patient while observing the inside of the body of the patient using the endoscope, the target tissue is located between the first arm and the second arm. In this state, when the operator pulls the operation wire toward the proximal end side, the first arm and the second arm are brought into a closed configuration in which the first arm and the second arm are in contact with each other so as to grasp the target tissue. When the operator further pulls the operation wire toward the proximal side, the target tissue is moved toward the proximal side while being grasped by the clip main body. Even when the target tissue is grasped by the clip main body, when the operator pushes the operation wire toward the distal end side, the first arm and the second arm of the clip main body enter the open configuration such that it is possible to grasp the target tissues again.

SUMMARY

According to an aspect of the present disclosure, an endoscope clip has a clip unit having an arm member that includes a plurality of arms; an operation wire having a distal end connected to the arm member, the operation wire configured to move toward a distal end side of the endoscope clip so as to cause the arm member to transition from a closed configuration in which the plurality of arms are closed to an open configuration in which the plurality of arms are separated from each other; and a restrictor, wherein the clip unit applies a biasing force to the operation wire toward the distal end side when the arm member is in the closed configuration, and when the arm member is in the closed configuration, the restrictor is configured to restrict the arm member from transitioning from the closed configuration to the open configuration by applying a force opposite to the biasing force to the operation wire, so as to restrict the movement of the operation wire toward the distal end side.

BRIEF DESCRIPTION OF DRAWINGS

FIG. 19A is a partial cross-sectional side view schematically showing a configuration of an endoscope clip according to a second modification example of the present embodiment.

FIG. 19C is a partial cross-sectional side view showing a state of releasing the restriction by the restriction portion of the endoscope clip according to the present modification example.

FIG. 22 is a flow-chart showing medical procedures by using the endoscope treatment tool according to the prior art.

DESCRIPTION OF EMBODIMENT

First Embodiment

Hereinafter, the configuration of the endoscope clip according to the first embodiment of the present invention will be described with reference from FIGS. 1A to 12.

The endoscope clip 1 according to the present embodiment is used by being inserted into a patient's body through a channel formed in an endoscope (not shown). In this specification, a side on which an endoscope operation section for the operator to operate the endoscope is located is defined as a proximal end side, and a side on which a distal end section of the endoscope inserted into the body is located is defined as a distal end side.

Figure 1A:
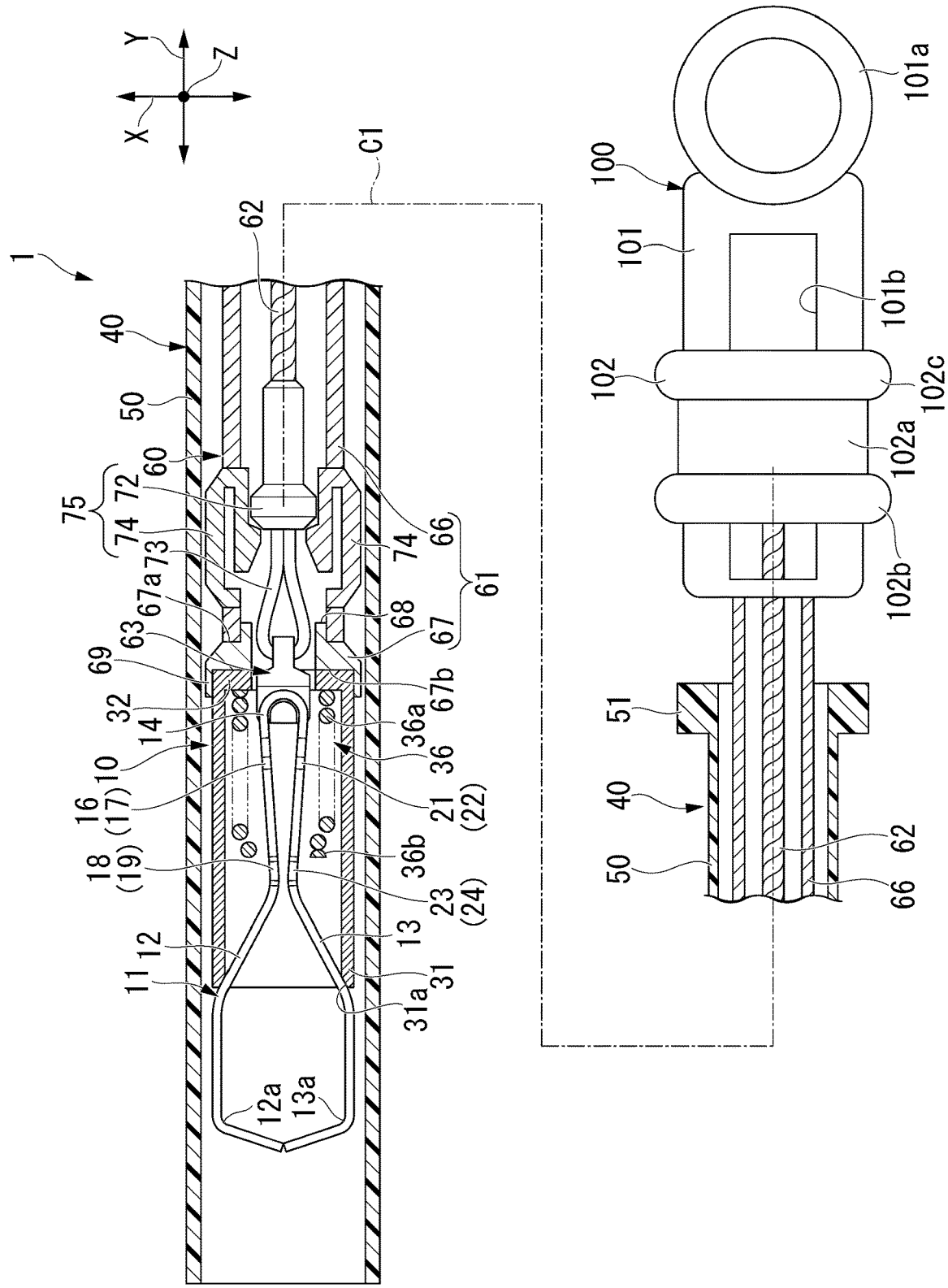
FIG. 1A is a partial cross-sectional side view schematically show an initial state of an endoscope clip according to a first embodiment of the present disclosure.

As shown in FIG. 1A, the endoscope clip 1 according to the present embodiment includes a clip unit (hereinafter, abbreviated as) "clip" 10 and a treatment tool main body (applicator) 40. The clip 10 is detachably connected to the distal end portion of the treatment tool main body 40. FIG. 1A is a partial cross-sectional side view of the clip 10 along a plane passing through an axis C1 of a pressing tube 31 described below. In this specification, for convenience of description, the axis C1 is regarded as an axis of the clip 10 and an insertion portion 60 described later.

In the present specification, as shown in FIG. 1A, an opposite direction X in which the first arm 12 and the second arm 13 of an arm member 11 of the clip 10 face each other, an axial direction Y parallel to the axis C1 of the pressing tube 31, and an orthogonal direction Z that is orthogonal to each of the opposite direction X and the axial direction Y are defined.

(Configuration of Clip 10)

As shown in FIG. 1A, the clip 10 is configured to include the arm member 11, a pressing tube 31, and an elastic member (a spiral spring) 36.

The pressing tube 31 is formed in a cylindrical shape and has an inner diameter into which a proximal end portion of the arm member 11 is able to enter. That is, a lumen into which the arm member 11 having the first arm 12 and the second arm 13 described below may enter is formed in the pressing tube 31. The elastic member 36 is arranged in the lumen of the pressing tube 31.

The arm member 11 has a first arm 12, a second arm 13, and a central portion 14. The first arm 12 and the second arm 13 are configured to extend from the proximal end side toward the distal end side and are arranged to face each other. The central portion 14 is located between the proximal end portion of the first arm 12 and the proximal end portion of the second arm 13. According to the present embodiment, as shown in FIG. 1A, the first arm 12 and the second arm 13 may be formed at positions to be line-symmetrical with respect to the axis C1.

According to the present embodiment, in a natural state, the first arm 12 and the second arm 13 are separated from each other, and a distance between the first arm 12 and the second arm 13 increases along a direction from the proximal end side toward the distal end side. In the present specification, the "natural state" refers to a state in which an external force is not applied to the arm member 11. For example, a state in which a force by an inner wall of the pressing tube 31 does not apply to the first arm 12 and the second arm 13 of the arm member 11 is the natural state. A claw 12a extending toward the second arm 13 side is formed at the distal end portion of the first arm 12. A claw 13a extending toward the first arm 12 side is formed at a distal end portion of the second arm 13.

The first arm 12 and the second arm 13 are formed to have a rounded shape that a cross-sectional shape orthogonal to a longitudinal direction at the distal end side is an arc shape. More specifically, each of central portions of the outer surfaces of the first arm 12 and the second arm 13 in the orthogonal direction Z that will be described below, is formed into a curved surface to form a convex portion that is convex outwardly toward the external side. The first arm 12 and the second arm 13 are configured in such a manner so as to have improved strength against bending and reduce frictional resistance to the outer sheath 50 described below so as to smoothly advance and retract.

Figure 1B:
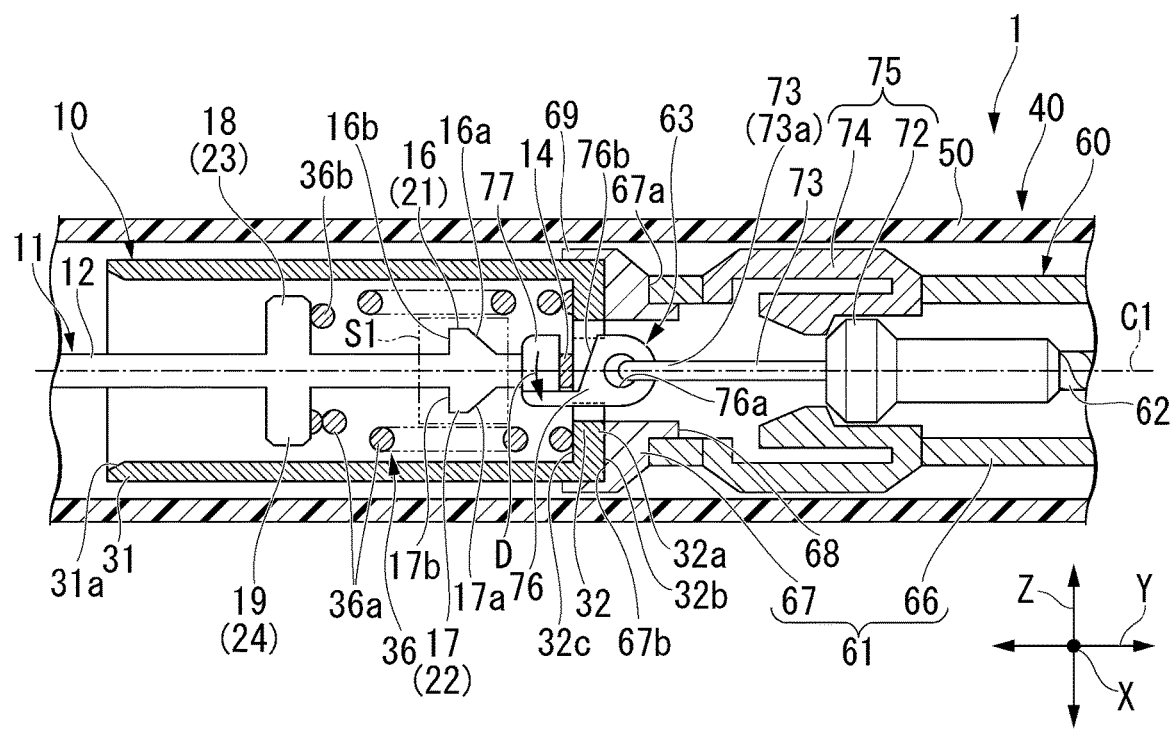
FIG. 1B is a partial cross-sectional planar view schematically show a distal end side of the endoscope clip in FIG. 1A.

In a planar view shown in FIG. 1B, two first engaged portions 16, 17 are provided at the proximal end portion of the first arm 12. The first engaged portions 16, 17 are provided on a reference plane S1 parallel to the axis line (central axis line) C1 of the pressing tube 31 so as to project from a lateral surface of the first arm 12 in the orthogonal direction Z. According to the present embodiment, the first engaged portions 16, 17 may project in directions opposite to each other and may be formed at positions to be line symmetrical with respect to the axis C1.

FIG. 1B is a partial cross-sectional planar view of the clip 10 viewed from a direction orthogonal to the reference plane S1. As shown in FIG. 1B, a proximal end surface 16a of the first engaged portion 16 is inclined to be separated from the first arm 12 (center axis C1) toward the distal end side. A distal end surface 16b of the first engaged portion 16 is orthogonal to the axial direction Y. A proximal end surface 17a of the first engaged portion 17 and the proximal end surface 16a of the first engaged portion 16 are line-symmetric with respect to the axis C1. The distal end surface 17b of the first engaged portion 17 and the distal end surface 16b of the first engaged portion 16 may be line-symmetric with respect to the axis C1.

As shown in FIGS. 1A and 1B, two protrusions 18, 19 are provided at a more distal end side of the first engaged portions 16, 17 of the first arm 12 respectively. As shown in FIG. 1B, the protrusions 18 and 19 protrude from a side surface of the first arm 12 in the orthogonal direction Z. According to the present embodiment, the protrusion 18 and the protrusion 19 may be line-symmetric with respect to the axis C1 in a planar view. Lengths of the protrusions 18, 19 protruding from the first arm 12 may be longer than the length of the first engaged portions 16, 17 protruding from the first arm 12 in the orthogonal direction Z, respectively.

As shown in FIG. 1A, second engaged portions 21, 22 and second protrusions 23, 24 which are formed in the same manner as the first engaged portions 16, 17 and the protrusions 18, 19 of the first arm 12 are provided in the second arm 13 (the second engaged portion 24 and the second protrusion 24 are not shown). In other words, the second engaged portions 21, 22 of the second arm 13 protrude from the side surface of the second arm 13 in the orthogonal direction Z which is a direction in which the second arm 13 is separated from the first arm 12. The projections 23, 24 of the second arm 13 project in the orthogonal direction Z from the side surface of the second arm 13 at a more distal end side of the second engaged portions 21, 22 of the second arm 13. The second engaged portions 21, 22 and the projections 23, 24 are arranged in the opposition direction X with respect to the first engaged portions 16, 17 and the projections 18, 19 respectively. In the planar view shown in FIG. 1B, the second engaged portions 21, 22 overlap the first engaged portions 16, 17, and the protrusions 23, 24 overlap the protrusions 18, 19, respectively.

These members including the arm member 11 that configure the clip 10 are made of a material such as a cobalt chrome alloy, titanium, or stainless steel. The clip 10 may also be configured to be observable under MRI (Nuclear Magnetic Resonance Imaging) fluoroscopy.

For example, the arm member 11 is formed by punching a plate material formed of a cobalt chrome alloy into a shape as expanding the first arm 12, the second arm 13, the central portion 14, the first engaged portions 16, 17, the second engaged portion 21, 22 and the protrusions 18, 19, 23, 24 into a flat shape. The arm member 11 is integrally formed by being bent at a connecting portion between the first arm 12 and the central portion 14, and a connecting portion between the second arm 13 and the central portion 14 to form a C-shape in a side view.

The first arm 12 and the second arm 13 of the arm member 11 have an elastic restoring force such that each distal end moves in a direction separating from each other, in other words, a direction in which the arm member 11 opens.

As shown in FIGS. 1A and 1B, an engaging portion 32 is formed on an inner wall of the proximal end portion of the pressing tube 31 so as to project over the whole circumference of the inner wall. Although it is not shown in the figures, an edge portion 32a of the engaging portion 32 on the axis C1 side is formed in a coaxial circular shape with respect to the pressing tube 31. As shown in FIG. 1B, the proximal end surface 32b (proximal end side end surface) and the distal end surface 32c (distal end side end surface) of the engaging portion 32 are orthogonal to the axial direction Y.

A portion of the first arm 12 closer to the proximal end side than the protrusions 18, 19, a portion of the second arm 13 closer to the proximal end side than the protrusions 23, 24, and the central portion 14 are capable of being inserted into the engaging portion 32. As described below, by an operator pulling back a slider 102 to the proximal end side, the first arm 12 and the second arm 13 move to the proximal end side together with the operation wire 62, and the portions at the proximal end side of the first arm 12 and the second arm 13 pass though the engaging portion 32 to be engaged at a position closer to the proximal end than the engaging portion 32.

As shown in FIG. 1B, a tapered surface 31a is formed on the inner wall of a distal end portion of the pressing tube 31 over the whole circumference. The tapered surface 31a has a diameter that increases toward the distal end side. According to the present embodiment, the pressing tube 31 and the engaging portion 32 may be integrally formed of a material such as 64 titanium alloy (Ti-6AL-4V) or cobalt chrome alloy.

As shown in FIGS. 1A and 1B, an end coil portion 36b is provided at the distal end portion of the elastic member 36. The end coil portion 36b is formed to have an inner diameter smaller than that of other portion of the elastic member 36.

The elastic member 36 is accommodated in the presser pipe 31 and has a distal end portion engaged to the projections 18, 19, 23, 24 and a proximal end portion engaged to the engaging portion 32. The proximal end portion of the elastic member 36 and the engaging portion 32 may be fixed by welding or the like.

In the elastic member 36, a portion in the first arm 12 that is closer to the proximal end than the protrusions 18 and 19, a portion of the second arm 13 that is closer to the proximal end than the protrusions 23 and 24, and the central portion 14 are capable of being inserted thereinto. When the protrusions 18, 19, 23, 24 move to the proximal end side, the protrusions 18, 19, 23, 24 are engaged to the end coil portion 36b of the elastic member 36. On the other hand, when the protrusions 18, 19, 23, 24 move to the proximal end side, the elastic member 36 is compressed by the protrusions 18, 19, 23, 24 in the axial direction Y. When the elastic member 36 is compressed, an elastic force that pushes the arm member 11 out of the pressing tube 31 in the axial direction Y is generated. Even when the end coil portion 36b is not included in the elastic member 36, the same effect may be achieved by attaching another member such as a washer or the like to the distal end of the elastic member 36.

(Configuration of Treatment Tool Main Body 40)

Next, a configuration of the treatment tool main body according to the present embodiment will be described.

As shown in FIGS. 1A and 1B, the treatment tool main body 40 includes an outer sheath 50, an insertion portion 60, and an operation portion 100. The outer sheath 50 can be formed of, for example, a fluororesin such as PTFE (polytetrafluoroethylene) or a resin material such as HDPE (high density polyethylene). An outer sheath operating portion 51 configured to operate the outer sheath 50 is disposed at a proximal end side of the outer sheath 50. According to the present embodiment, for example, it is possible to pull back the outer sheath 50 with respect to the insertion portion 60 of the treatment tool main body 40 by operating the outer sheath operating portion 51.

The insertion portion 60 in advanceable and retractable in the outer sheath 50. The operation portion 100 is attached to a proximal end portion of the insertion portion 60.

(Configuration of Insertion Portion 60)

The insertion portion 60 of the treatment tool main body 40 includes a sheath 61, an operation wire (wire) 62, a connection member 63, and a loop portion 73. The operation wire 62 is inserted into the sheath 61 so as to be advanceable and retractable in the sheath 61. The operation wire 62 is configured to transmit a force by which the operator operates the operation portion 100 at the proximal end side (for example, an operation of pushing the slider 102 and pulling back the slider 102) to the clip 10. The connection member 63 is connected to the distal end portion of the operation wire 62. The connection member 63 is configured to be rotatable around an axis parallel to the opposite direction X with respect to the operation wire 62.

The sheath 61 has a coil sheath 66, a distal member (stopper engaging portion) 67 fixed to the distal end portion of the coil sheath 66, and a fixing member (engaged portion) 74 disposed on the inner circumferential surface of the coil sheath 66.

The coil sheath may be formed of stainless steel such as SUS301 having high compressive strength. The coil sheath 66 may be configured by using a coil formed by closely winding a wire (not shown) in the axial direction Y. The coil sheath 66 has flexibility while being strong against a compressive force in the axial direction Y. The inner diameter of the coil sheath 66 may be substantially the same with the inner diameter of the elastic member 36.

According to the present embodiment, the distal member 67 may be formed in a cylindrical shape and from, for example, stainless steel or the like. An inner diameter of the distal member 67 is smaller than the inner diameter of the coil sheath 66. An outer diameter of the distal member 67 is larger than the outer diameters of the coil sheath 66 and the pressing tube 31. A concave portion 67a is formed on the outer circumferential surface of a proximal end portion of the distal member 67 by reducing an outer diameter thereof. The distal member 67 and the coil sheath 66 are fixed by laser welding or the like in a state in which the distal end of the coil sheath 66 is engaged with the concave portion 67a.

A step portion 68 is formed in a connection portion of the coil sheath 66 and the distal end portion 67 on an inner circumferential surface of the distal end portion of the sheath 61 by reducing the inner diameter of the distal member 67 closer to the distal end than the coil sheath 66. The inner diameter of the distal member 67 may be set to cause the distal member 67 not to engage with the first engagement portions 16, 17 and the second engaged portions 21, 22.

A step difference is formed on the whole circumference on the inner circumferential surface of the distal end portion of the distal member 67. In the step difference, a surface facing the distal end side is a distal end support surface (distal end surface) 67b. A support portion 69 is formed at a more distal end side than the distal end support surface 67b. According to the present embodiment, the support portion 69 is formed in a cylindrical portion. An inner diameter is slightly larger than the outer diameter of the pressing tube 31 so as to be capable of accommodating the proximal end of the pressing tube. The distal end support surface 67b is contactable with the proximal end surface of the pressing tube 31. The clip 10 is disposed at the distal end side of the sheath 61. The support portion 69 is possible to support the outer circumferential surface of the pressing tube 31 being in contact with the distal end support surface 67b.

According to such configuration, the unstableness of the clip 10 with respect to the support portion 69 can be suppressed as small as possible, and a certain degree of inclination of the clip 10 with respect to the support portion 69 may be allowed. Accordingly, the endoscope clip 1 can be smoothly inserted even in a bent shape of an endoscope channel or the like.

Figure 2:
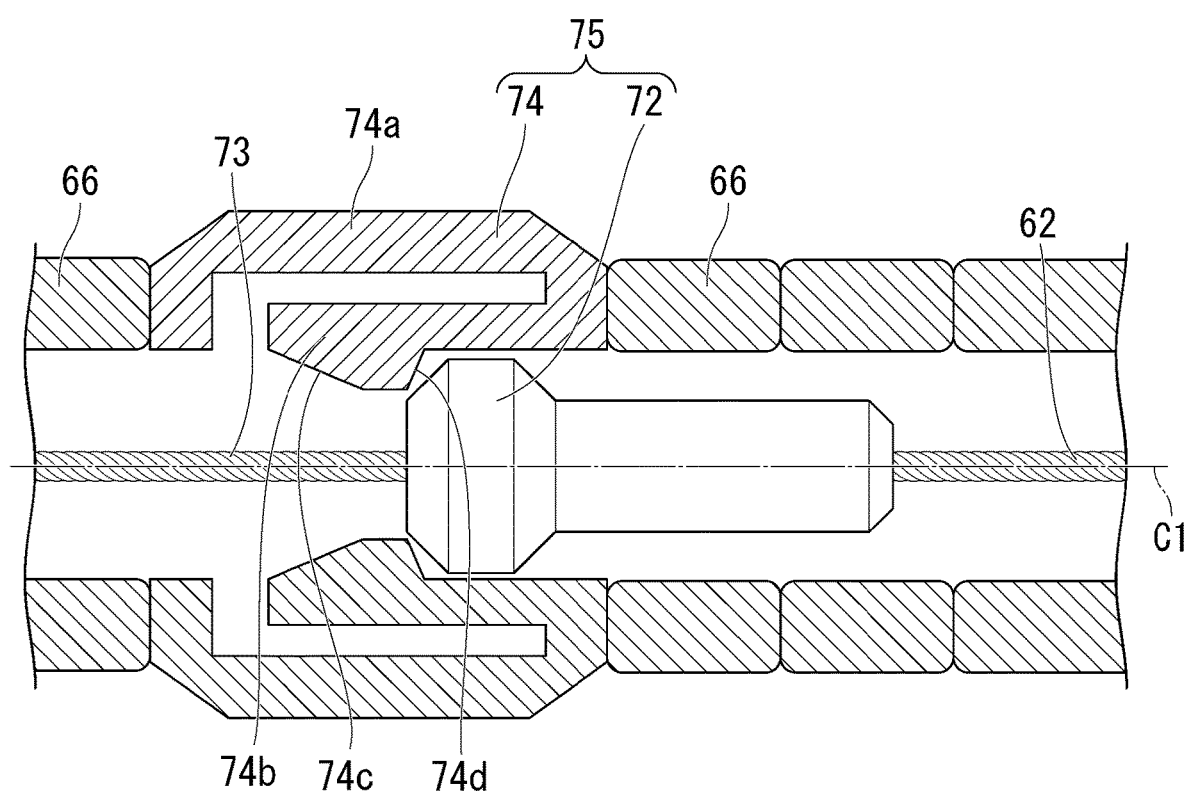
FIG. 2 is an enlarged cross-sectional view showing a restriction portion of the endoscope clip according to the present embodiment.

As shown in FIG. 2, according to the present embodiment, the fixing member (engaged portion of the restriction portion) 74 is provided on the inner circumferential surface of the distal end side of the sheath 61 so as to project toward the axis C1. For example, the fixing member 74 may be fixed by welding the distal end and the proximal end to the wire forming the coil sheath 66 along the axial direction Y. That is, the fixing member 74 may be formed integrally with the coil sheath 66.

According to the present embodiment, an example in which the fixing member 74 and the coil sheath 66 are integrally configured is described; however, the fixing member 74 is not limited to this configuration. For example, the fixing member 74 may be fixed to the inner circumferential surface on the distal end side of the coil sheath 66 by a method such as welding, bonding or the like, wherein the inner circumferential surface of the coil sheath 66 is formed by tightly winding the wire in the axial direction Y.

According to the present embodiment, as shown in FIG. 2, the fixing member 74 is not limited to the example in which the fixing member 74 is sandwiched between the wires forming the coil sheath 66. For example, the fixing member 74 may be arranged at the distal end side of the coil-sheath 66, and the proximal end of the fixing member 74 along the axial direction Y may be fixed to the wire forming the coil sheath 66 by a method such as welding, bonding or the like. According to the present embodiment, the material used to form the fixing member 74 is not particularly limited. For example, in order to ensure durability, the fixing member 74 may be formed of the same metal material as that of the pressing tube 31 and the engaging portion 32.

As shown in FIG. 2 as a cross-sectional view of the fixing member 74, the fixing member 74 according to the present embodiment is configured to have a supporting portion 74a and a deforming portion 74b. The supporting portion 74a is formed radially outward of the deforming portion 74b with respect to the axis C1. The supporting portion 74a is configured that the distal end and the proximal end of the supporting portion 74a are fixed to the wire forming the coil sheath 66.

The deforming portion 74b has a proximal end portion connected to the proximal end portion of the supporting portion 74a, and a portion located closer to the distal end side than the proximal end portion is formed to be apart from the supporting portion 74a by a certain distance. That is, the deforming portion 74b forms a gap with the supporting portion 74a at the certain distance outwardly in the radial direction with respect to the axis C1.

The outer diameter of the fixing member 74 is defined as the maximum width of the supporting portion 74a in the radial direction orthogonal to the central axis C1. According to the present embodiment, for example, the outer diameter of the fixing member 74 may be slightly larger than the outer diameter of the coil sheath 66.

As shown in FIG. 2, the deforming portion 74b of the fixing member 74 is formed that at least a portion of the deforming portion projects toward the axis C1. In other words, at least a portion of the deforming portion 74b of the fixing member 74 is formed to project inward in the radial direction around the axis C1. The deforming portion 74b is configured by a pair of claws that are arranged at positions opposite to each other to sandwich the axis C1 therebetween. A distance between the pair of claws (that is, a width of the space between the pair of claws) is smaller than the inner diameter of the coil sheath 66 and the outer diameter of the stopper 72 described below. In other words, the fixing member 74 has an inner cavity with an inner diameter smaller than the inner diameter of the coil sheath 66 and the outer diameter of the stopper 72 described below.

According to the present embodiment, the example in which the deforming portion 74b is configured by a pair of claws has been described; however, the present disclosure is not limited thereto. For example, the deforming portion 74b may be configured from a single claw. In this case, the width of the inner cavity of the fixing member 74 (the inner cavity with a width smaller than the inner diameter of the coil sheath 66 and the outer diameter of the stopper 72 described below) is defined by the single claw. As shown in FIG. 2, in the deforming portion 74b of the fixing member 74, a distal end 74c and a proximal end 74d are formed in an inclined surface so as to engage with a stopper 72 described below.

The deforming portion 74b of the fixing member 74 according to the present embodiment may be rotated outwardly in the radial direction with the connection portion of the supporting portion 74a and the deforming portion 74b as a fulcrum and elastically deformed by the operator pushing the slider 102 of the operation portion 100 such that the deforming portion 74b is pressed into the stopper 72 in a state in which the fixing member 74 and the stopper 72 are in contact state (engagement).

For example, the operation wire 62 is formed of a metal single wire or a twisted wire. A distal end of the operation wire 62 is connected to the proximal end of the stopper 72. That is, According to the present embodiment, the operation wire 62 and the stopper 72 may move together. The loop portion 73 is connected to the distal end portion of the stopper 72.

For example, the stopper (engagement portion or engaging portion) 72 is formed of metal and in a cylindrical shape. The outer diameter of the stopper 72 is smaller than the inner diameter of the coil sheath 66 and larger than the inner diameter of the distal member 67. As described above, the outer diameter of the stopper 72 is larger than the width of the inner cavity formed inside the fixing member 74.

The stopper 72 has a tapered distal end surface and a proximal end surface at the distal end and the proximal end along the axial direction Y respectively.

According to the present embodiment, the stopper 72 has the above-described configuration such that as described below, in a state in which the operator does not apply any operating force, due to the elastic force of the elastic member 36 disposed in the pressing tube 31, the stopper 72 is biased to the distal end side and may be engaged with the fixing member 74. By the operator pushing the slider 102 of the operation portion 100, the stopper 72 may move toward the distal end side to climb on and overcome the fixing member 74. By the operator pushing the slider 102 of the operation portion 100, the stopper 72 comes into contact with the step portion 68 of the distal member 67 such that the arm member 11 of the clip 10 may be transitioned to an open configuration in which the first arm and the second arm are spaced apart from each other.

The loop portion 73 is formed by folding back one wire 73a. The wire 73a has a folded-back portion located at the distal end side, and both end portions at the proximal end side are fixed to the stopper 72 by brazing, resistance welding or the like.

As shown in FIG. 1B, the connection member 63 has a hook 77 at the distal of the connecting portion main body 76 and a through hole 76a formed at the proximal end of the connecting portion main body 76. An inclined surface 76b is formed on a surface of the connecting portion main body 76 being opposite to the hook 77.

The connection member 63 is connected to the loop portion 73 and rotatable around an axis parallel to the opposite direction X (rotatable around the arrowhead direction D in FIG. 1B) by inserting the folded-back portion of the wire 73a of the loop portion 73 into the through hole 76.

The width of the connection member 63 is the outer diameter in the direction orthogonal to the central axis C1 of the connecting portion main body 76 when the hook 77 is arranged on the distal side. The width of the connection member 63 is slightly smaller than the inner diameter of the elastic member 36, the inner diameter of the coil sheath 66, and the inner diameter of the distal member 67. That is, the connection member 63 cannot rotate with respect to the loop portion 73 in the pressing tube 31 and in the sheath 61 when the hook 77 is on the distal end side. In other words, the relative movement of the arm member 11 and the hook 77 in the radial direction is restricted by the pressing tube 31 and the sheath 61.

The above-mentioned recitation □the connection member 63 cannot rotate with respect to the loop portion 73□ means that the connection member 63 cannot rotate with respect to the loop portion 73 until the engagement between the hook 77 and the central portion 14 is released. Accordingly, the recitation □the connection member 63 cannot rotate with respect to the loop portion 73□ does not literally mean that the connection member 63 cannot rotate with respect to the loop portion 73 at all.

By disposing the central portion 14 between the hook 77 of the connection member 63 and the inclined surface 76b, the hook 77 can be engaged with the central portion 14. When the hook 77 rotates in the direction D with respect to the loop portion 73, the engagement between the hook 77 and the central portion 14 is released (see FIG. 10). That is, the connection member 63 is detachably connected to the arm member 11. The connection member 63 is located inside the presser pipe 31.

(Configuration of Restriction Portion 75)

In the present embodiment, a configuration including both of the stopper 72 and the fixing member 74 is defined as the restriction portion (restrictor) 75 of the endoscope clip 1, the stopper 72 is defined as an engaging portion of the restriction portion 75, and the fixing member 74 is defined as an engaged portion of the restriction portion 75.

As shown in FIGS. 1A and 1B, in a state in which the stopper 72 is located closer to the proximal end side than the fixing member 74 and the operator does not grasp the slider 102, due to the elastic force of the elastic member 36 disposed in the pressing tube 31, the stopper 72 moves toward the distal end side along the axial direction Y and abut (engage) with the fixing member 74.

According to the present embodiment, the stopper 72 and the fixing member 74 are engaged with each other such that the elastic force applied on the stopper 72 by the elastic member 36 and the fixing force applied on the stopper 72 by the fixing member 74 are balanced. The fixing force by the fixing member 74 refers to a force for preventing (restricting) the stopper 72 from moving to the distal end side by the fixing member 74 by the stopper 72 and the fixing member engaging with each other and pressing against each other.

More specifically, when the elastic force of the elastic member 36 applies on the stopper 72, the stopper 72 is biased toward the distal side, and when the stopper 72 abuts on the fixing member 74, a force for pushing the fixing member 74 toward the distal end side is generated. When the fixing member 74 receives this force, the deforming portion 74b is elastically deformed outwardly in the radial direction with respect to the axis C1 such that the inner diameter of the inner cavity increases and a repellent force (fixing force) that opposes the elastic force of the elastic member 36 is generated. According to the present embodiment, the fixing force generated when the inner diameter of the fixing member 74 becomes equal to the outer diameter of the stopper 72 is set to be equal to or larger than the elastic force of the elastic member 36. Accordingly, in a state in which the operator does not operate the slider 102, that is, a state where an external force does not apply on the operation wire 62, it is impossible for the stopper 72 to climb on and overcome the fixing member 74 along the axial direction Y to move to the distal end side.

In other words, the engagement between the stopper 72 and the fixing member 74 is maintained and the movement of the operation wire 62 toward the distal end side is restricted in a state in which the operating force by the operator does not apply on the slider 102.

According to the present embodiment, the restriction portion 75 is configured to restrict the movement of the operation wire 62 of the endoscope clip 1 toward the distal end side in a natural state in which no external force applies. As described below, the restriction portion 75 is provided to restrict the transition of the arm member 11 of the clip 10 from the closed configuration to the open configuration in a natural state in which no external force applies. According to the present disclosure, the closed configuration of the arm member 11 is defined as a state in which the first arm 12 and the second arm 13 are in contact with each other or a distance between the distal end of the first arm 12 and the distal end of the second arm 13 is substantially zero. The state in which the distance between the distal end of the first arm 12 and the distal end of the second arm 13 is substantially zero refers to that the first arm 12 and the second arm 13 are separated from each other and the claw 12a of the first arm 12 and the claw 12b of the second arm 13 are not oriented toward the front side.

Details will be described below, however when the operator operates (for example, pushes) the slider 102 to apply a force larger than the elastic force of the elastic member 36 on the operation wire 62, the restriction by the restriction portion 75 is released, and the operation wire 62 is movable to the distal end side.

According to the present embodiment, it is preferable that the fixing member 74 of the restriction portion 75 is arranged closer to the proximal end than the elastic member 36 inside the pressing tube 31. More preferably, the fixing member 74 of the restriction portion 75 is arranged at a position closer to the proximal end than the distal end opening of the sheath 61. For example, according to the present embodiment, the fixing member 74 of the restriction portion 75 may be arranged at a position within about 1 cm from the distal end opening of the sheath 61 toward the proximal end side. On the other hand, as described above, the stopper 72 of the restriction portion 75 may move toward the distal end until the stopper 72 comes into contact with the step portion 68 formed on the proximal end side of the distal end member 67.

By configuring the fixing member 74 of the restriction portion 75 in this manner, a distance between a position where the stopper 72 is engaged with the fixing member 74 and a position of the arm member 11 becomes small. According to the configuration of the endoscope clip 1 according to the present embodiment, even when the endoscope clip 1 is inserted into a luminous cavity having a complicated shape and the coil sheath 66 is meandering, it is possible to suppress a change in a path length between the stopper 72 and the arm member 11. As a result, the closed configuration of the arm member 11 may be more reliably maintained due to the engagement of the fixing member 74 and the stopper 72.

(Configuration of Operation Unit 100)

As shown in FIG. 1A, the operation unit 100 has an operation unit main body (handle) 101 and a slider 102.

The operation portion main body 101 is attached to the proximal end of the coil sheath 66. The operation portion main body 101 is formed in a rod shape extending in the axial direction Y, and a finger hook portion 101a is disposed at a proximal end portion of the operation portion main body. A slit 101b extending in the axial direction Y is formed in the operation unit main body 101.

The slider 102 is inserted into the operation portion main body 101. The slider 102 is slidable (advances and retracts) in the axial direction Y with respect to the operation unit main body 101. The proximal end of the operation wire 62 is connected to the slider 102. In the clip 10 according to the present embodiment, the operation wire 62 advances and retracts by advance operation and retraction operation of the slider 102 along the axial direction Y. A diameter expansion member 72, the loop portion 73, and the arm member 11 of the clip 10 disposed on the distal end side of the operation wire 62 are advanceable and retractable. As a result, a pair of first arm 12 and second arm 13 of the arm member 11 may be opened or closed.

The slider 102 is formed in a cylindrical shape. On an outer circumferential surface of the slider 102, a recess 102a is formed over the whole circumference. On the slider 102, a flange portion 102b, a recess portion 102a, and a flange portion 102c are formed in this sequence from the distal end side to the proximal end side in the axial direction Y. The pair of flange portions 102b and 102c have an elliptical shape when viewed in the axial direction Y. As a result, the slider 102 is configured to be easy to be grasped and space-saving may be achieved at the time of packaging the operation portion 100 of the endoscope clip 1.

The slider 102 is configured to restrict the movement range of the slider 102 with respect to the operation main body 101 in the axial direction Y by engaging with the slit 101b of the operation portion main body 101.

(Initial State of the Endoscope Clip 1)

Next, a medical procedure for ligating a target tissue T using the endoscope clip 1 having the above-described configuration will be described.

In an initial state before the procedure is started, when the endoscope clip 1 is provided to the operator, as shown in FIG. 1A, the clip 10 is attached to the treatment instrument body 40 and covered with the outer sheath 50.

As shown in FIG. 1A and FIG. 1B, in the initial state, the elastic member 36 of the clip 10 has a configuration in which the strands 36a adjacent to each other in the axial direction Y are separated from each other and are slightly compressed in the axial direction than the natural state (a state in which no external force applies). Accordingly, due to the elastic force of the elastic member 36, the pressing tube 31 is held by the distal end member 67 in a state where the proximal end surface is in contact with the distal end supporting surface 67b of the distal end member 67. As described above, in the natural state, the elastic force of the elastic member 36 applies on the arm member 11 of the clip 10 such that the elastic force of the elastic member 36 has a function of pushing the arm member 11 out of the pressing tube 31. That is, when the elastic force of the elastic member 36 is applied to the arm member 11, the stopper 72 is moved to the distal side. As a result, the stopper 72 and the fixing member 74 come into contact with each other and press each other.

More specifically, in the endoscope clip 1 in the initial state, the stopper 72 is located closer to the proximal end side than the fixing member 74 in the sheath 61. Accordingly, due to the elastic force of the elastic member 36, the stopper 72 is biased toward the distal end side along the axial direction Y and moved to the distal end side until coming in contact with the fixing member 74. When the stopper 72 abuts (engages) with the fixing member 74, the elastic force of the elastic member 36 and the fixing force generated by the elastic deformation of the fixing member 74 oppose and balance each other, such that the state in which the stopper 72 and the fixing member 74 are engaged with each other is maintained. The deforming portion 74b of the fixing member 74 is pressed by the stopper 72. In this state, the distal end surface of the slider 102 of the operation portion 100 at the proximal end side is separated from the proximal end surface of the slit 101b of the operation portion main body 101 at a certain distance.

As shown in FIG. 1A, the proximal end portion of the first arm 12, the proximal end portion of the second arm 13, and the central portion 14 may be positioned at the distal end side more than the engaging portion 32 in the pressing tube 31. When the stopper 72 abuts the fixing member 74, the first engaged portions 16, 17 and the second engaged portions 21, 22 of the arm member 11 are located on the distal end side more than the engaging portion 32. At this time, the first engaged portions 16, 17 and the second engaged portions 21, 22 are not in contact with the engaging portion 32 of the pressing tube 31. A portion between the distal end and the proximal end each of the first arm 12 and the second arm 13 of the arm member 11 is in contact with a tapered surface 31a formed over the whole circumference of the inner wall of the distal end portion of the pressing tube 31. The first arm 12 and the second arm 13 of the arm member 11 are spaced apart from the inner wall of the outer sheath 50 with a space therebetween. In the arm member 11, the distal end of the first arm 12 and the distal end of the second arm 13 are in contact with each other, or the distance between the distal end of the first arm 12 and the distal end of the second arm 13 is substantially zero. As described above, according to the present embodiment, such a state is the closed configuration of the clip 10.

At this time, the operator may adjust an orientation of the clip 10 by rotating the operation wire 62 with respect to the sheath 61 so as to rotate the arm member 11 around the axis C1 with respect to the pressing tube 31. According to the present embodiment, since the edge portion 32a of the engaging portion 32 is formed in a circular shape coaxial with the pressing tube 31, even when the arm member 11 is rotated around the axis C1, the engagement between the engaging portion 32 and the first engaged portions 16, 17 and the second engaged portions 21, 22 is suitably maintained.

When using the endoscope clip 1, the operator inserts an endoscope (not shown) into the body of the patient. Subsequently, the operator inserts the endoscope clip 1 from the proximal end portion of the channel of the endoscope, and projects the outer sheath 50 of the endoscope clip 1 from the distal end portion of the channel of the endoscope.

(Restriction State of the Endoscope Clip 1)

Figure 3:
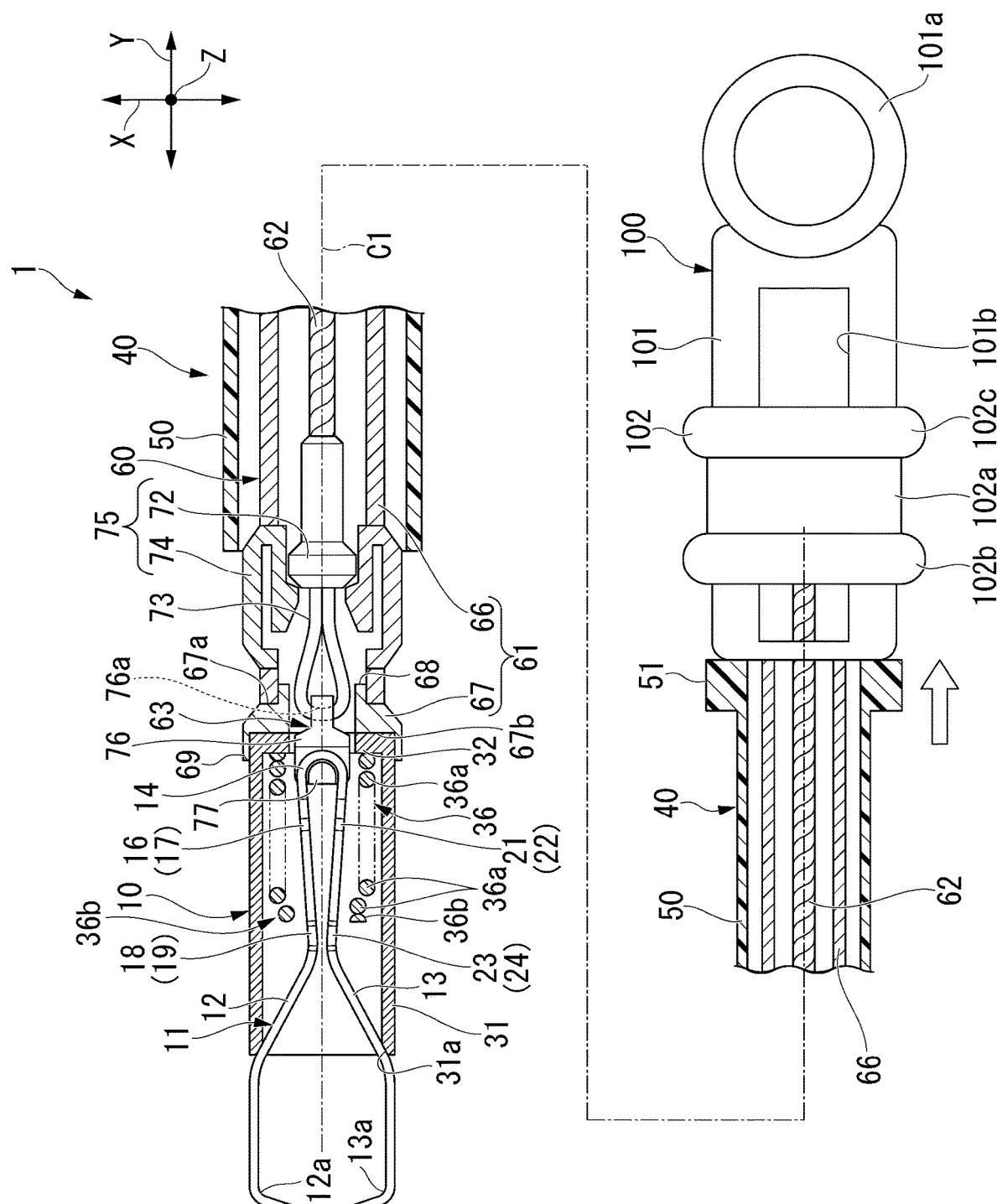
FIG. 3 is a partial cross-sectional view schematically show an initial state of the endoscope clip according to the present embodiment.

Subsequently, as shown in FIG. 3, the operator operates the outer sheath operating portion 51 of the operating portion main body 101 to pull back the outer sheath 50 with respect to the insertion portion 60 of the treatment tool main body 40, and causes the first arm 12 and the second arm 13 of the arm member 11 to be projected from the distal end portion of the channel of the endoscope.

As described above, in the endoscope clip 1 according to the present embodiment, the fixing force generated when the width of the inner cavity of the fixing member 74 becomes equal to the outer diameter of the stopper 72 is set to be equal to or larger than the elastic force of the elastic member 36. Accordingly, even in a state in which the first arm 12 and the second arm 13 of the arm member 11 are projected from the distal end portion of the channel of the endoscope, the state in which the stopper 72 and the fixing member 74 are engaged is maintained. That is, the fixing member 74 of the restriction portion 75 and the stopper 72 are engaged with each other, and the movement of the operation wire 62 toward the distal end side is restricted.

As a result, the movement of the arm member 11 toward the distal side is restricted, and the closed configuration of the arm member 11 is maintained. In this state, the first engaged portions 16, 17 and the second engaged portions 21, 22 of the arm member 11 are located at the distal end side more than the engaging portion 32 in the pressing tube 31.

(Restriction-Release State of Endoscope Clip 1)

Subsequently, the operator confirms the target tissue T using the endoscope (not shown) while releasing the restriction of the movement of the operation wire 62 toward the distal end side due to the restriction portion 75 of the endoscope clip 1.

Figure 4:
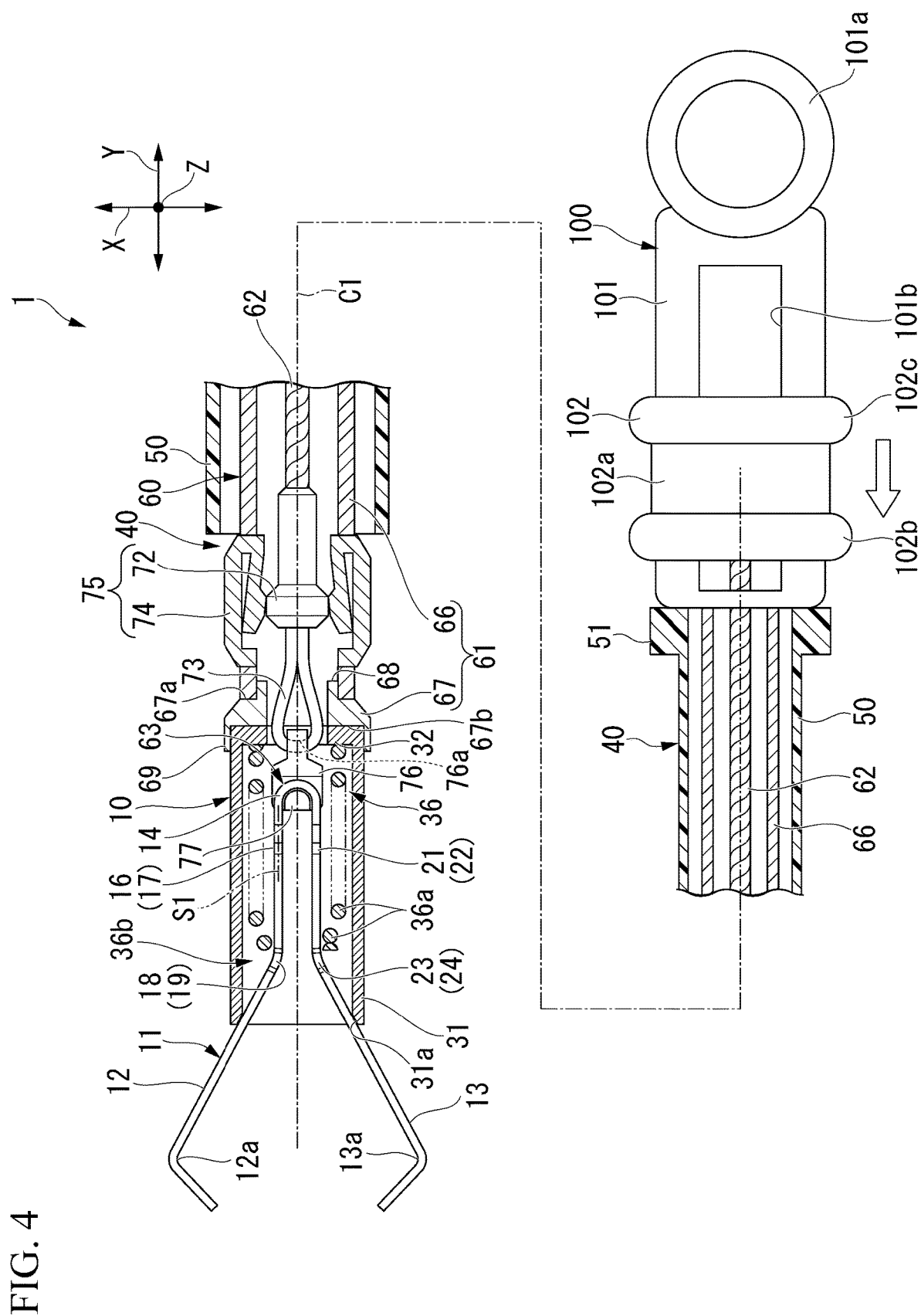
FIG. 4 is a partial cross-sectional view showing an operation to open an arm member of the endoscope clip according to the present embodiment.
Figure 5:
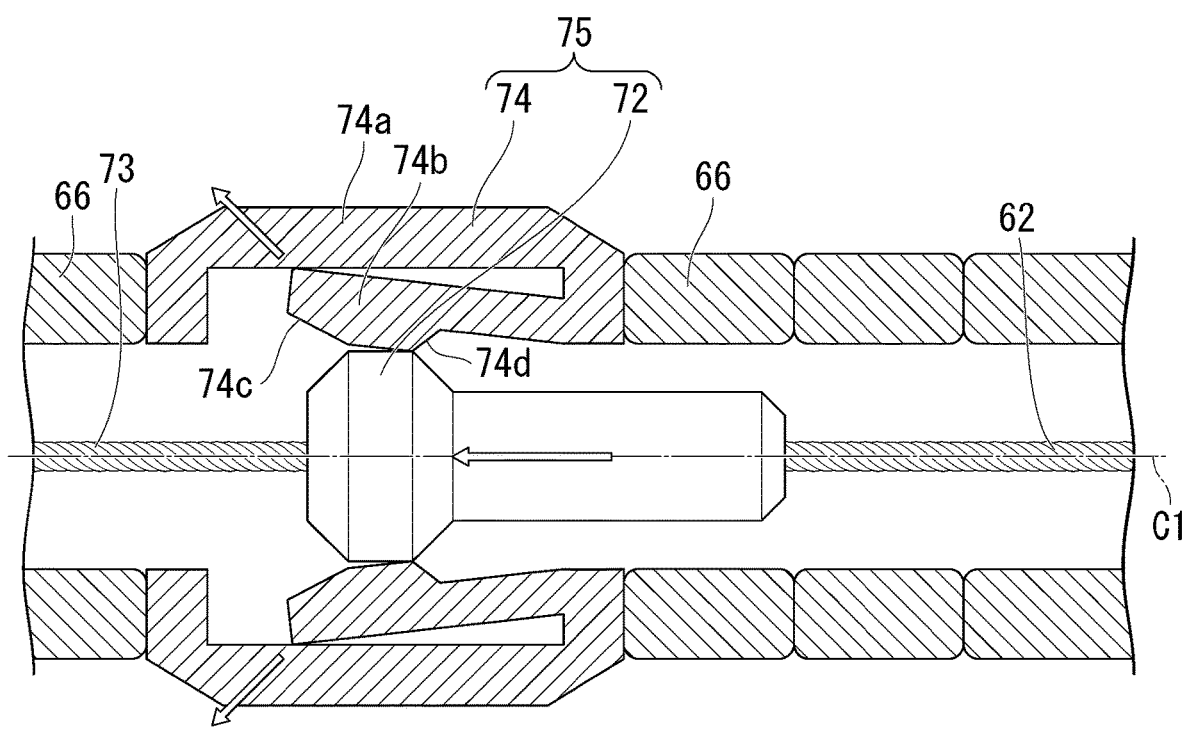
FIG. 5 is an enlarged cross-sectional view showing a state of the restriction portion of the endoscope clip in FIG. 4.

Specifically, when the operator pushes the slider 102 toward the distal end side, the operating force of the operator applies on the stopper 72 via the operation wire 62 such that the deforming portion 74b of the fixing member 74 rotates outwardly in the radial direction with respect to the axis C1 to be further elastically deformed. In this state, a sum of the operating force of the operator and the elastic force of the elastic member 36 becomes equal to or larger than the maximum magnitude of the fixing force of the fixing member 74 of the restriction portion 75, that is, the maximum magnitude of a restriction force provided by the engagement of the stopper 72 and the fixing member 74. As shown in FIGS. 4, 5, the stopper 72 is pushed into the inner cavity of the fixing member 74 by the operator pushing the slider 102 while contacting the elastically deformed deforming portion 74b of the fixing member 74.

As shown in FIGS. 4 and 5, while the stopper 72 of the restriction portion 75 and the fixing member 74 are engaged with each other, the operator may push the slider 102 to move the operation wire 62 and the stopper 72 toward the distal end side with respect to the fixing member 74. At this time, the connecting portion 63 and the arm member 11 connected to the distal end side of the operation wire 62 are moved toward the distal end side together with the operation wire 62. The first arm 12 and the second arm 13 of the arm member 11 are in contact with the tapered surface 31*a* formed at the distal end portion of the pressing tube 31 and the distal ends thereof are in a separating state. As the operator pushes in the slider 102, the first arm 12 and the second arm 13 of the arm member 11 are separated from each other such that the distance therebetween increases. That is, the operator may push the slider 102 so as to cause the arm member 11 to be transitioned from the closed configuration to the open configuration.

However, as shown in FIGS. 4, 5, the distance between the first arm 12 and the second arm 13 of the arm member 11 is smaller than the maximum possible opening width.

According to the present embodiment, since the elastic force of the elastic member 36 and the restriction force of the restriction portion 75 are in balance, if the sum of the operating force by the operator pushing the slider 102 and the elastic force of the elastic member 36 slightly exceeds the restriction force by the restriction portion 75, the restriction by the restriction portion 75 may be released. In other words, according to the present embodiment, there is no necessary that the operating force exceeds the elastic force of the elastic member 36, and the magnitude of the operating force can be easily controlled.

As shown in FIGS. 4, 5, the operator may once pull the slider 102 toward the proximal end side during the process in which the stopper 72 contacts the fixing member 74 and moves toward the distal end side with respect to the fixing member 74 by the operator pushing the slider 102. Accordingly, the stopper 72 may move to the proximal end side with respect to the fixing member 74 while contacting the fixing member 74. That is, the first arm 12 and the second arm 13 of the arm member 11 may be transitioned from the open configuration to the closed configuration by the operator pulling the slider 102. As a result, for example, when the arm member 11 is opened too much and the opening width of the arm member 11 is to be adjusted according to the target tissue T to be treated, the opening width of the arm member 11 may be readjusted again. For example, in a case when the arm member 11 is moved in the body in order to place the clip 10 at a position different from the treatment target, it is possible to prevent the opened first arm 12 and the second arm 13 of the arm member 11 from unintentionally contacting the body wall and the handling of the treatment tool becomes easy.

Figure 6:
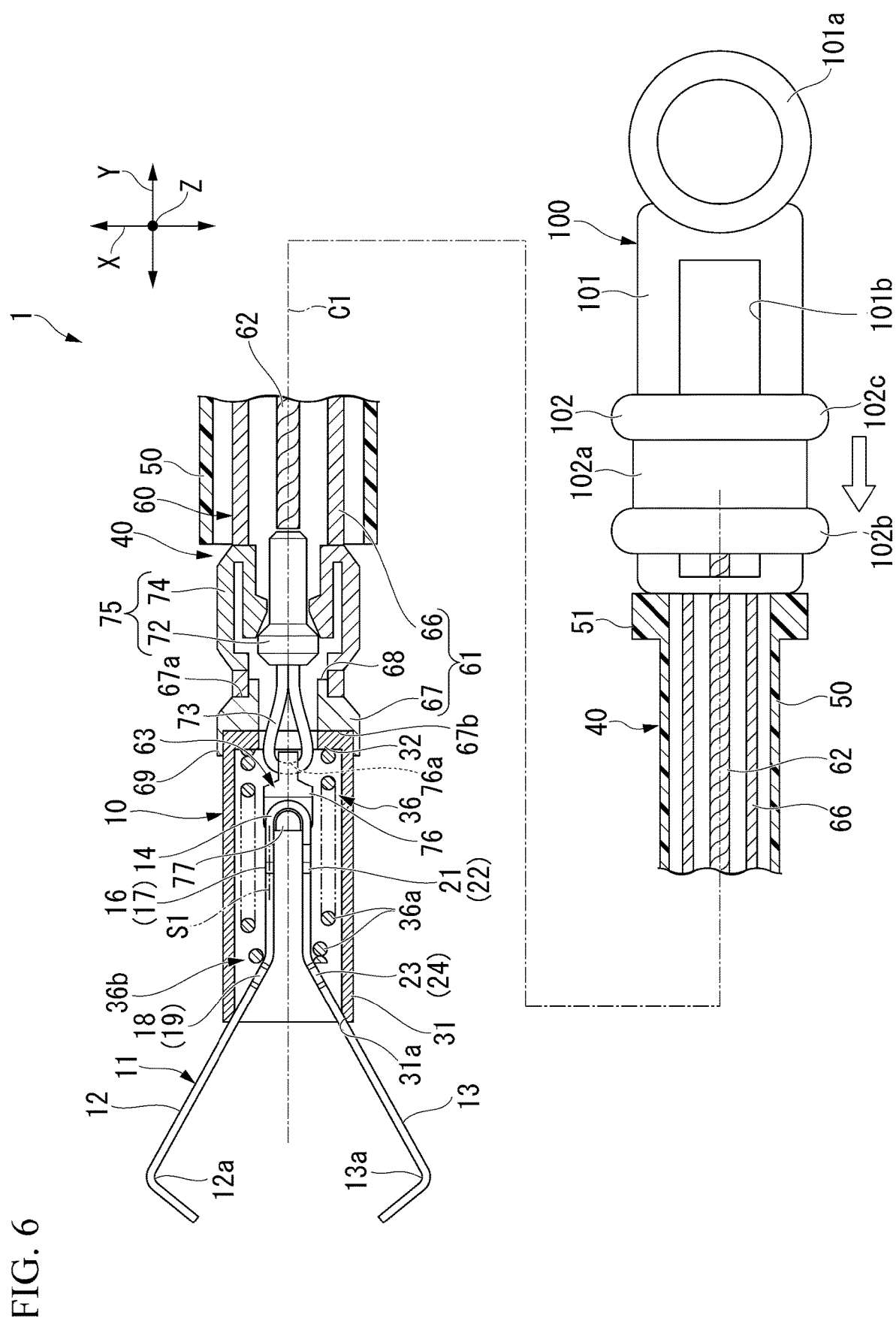
FIG. 6 is a partial cross-sectional view showing a state in which restriction due to the restriction portion of the endoscope clip according to the present embodiment is released.
Figure 7:
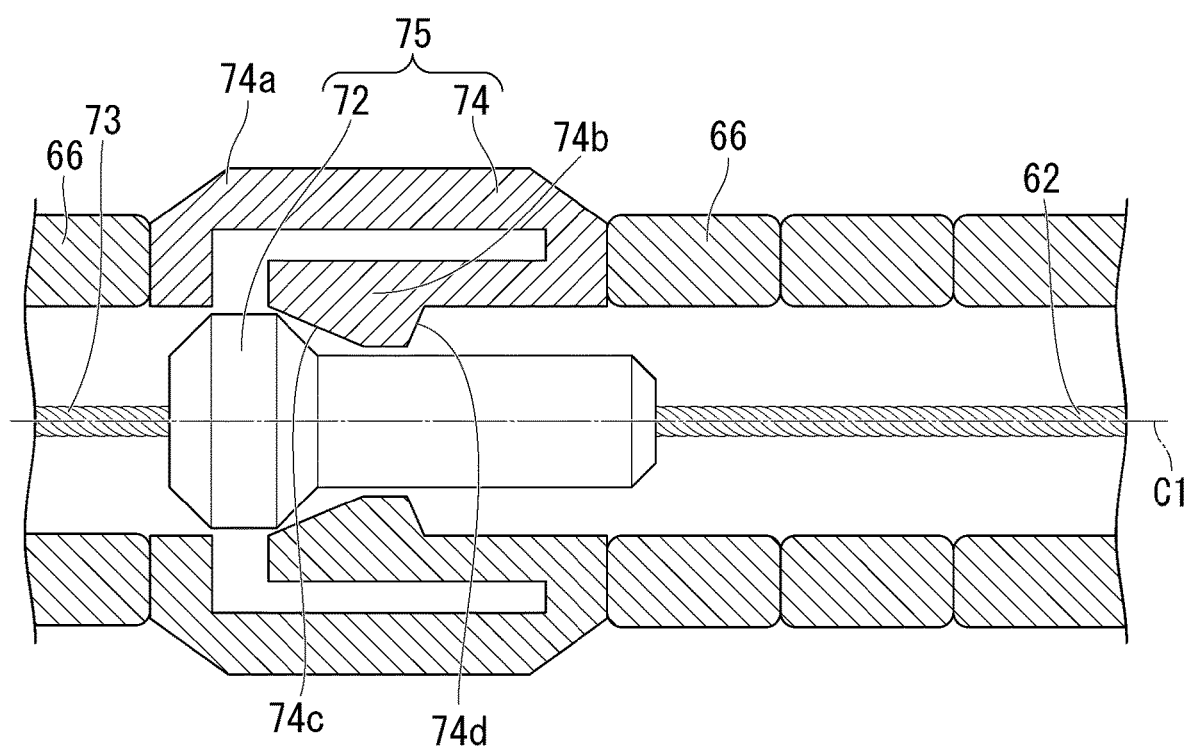
FIG. 7 is an enlarged cross-sectional view showing a state of the restriction portion of the endoscope clip in FIG. 6.

As shown in FIGS. 4, 5, when the operator continuously pushes the slider 102, the operation wire 62, the connecting portion 63, and the arm member 11 move toward the distal end side, and the opening width of the first arm 12 and the second arm 13 of the arm member 11 increases. As a result, as shown in FIG. 6, the stopper 72 climbs on and overcome the deforming portion 74*b* of the fixing member 74 to be positioned at the distal end side more than the deforming portion 74*b* of the fixing member 74. At this time, the engagement state between the stopper 72 and the fixing member 74 is released, and the deforming portion 74*b* of the fixing member 74 is restored to the initial shape. In other words, the restriction of the movement of the operation wire 62 toward the distal end side is released by applying a force to the operation wire 62 which is larger than the fixing force generated by engaging the stopper 72 of the restriction portion 75 and the fixing member 74 to cause the fixing member 74 to be elastically deformed.

In this state, the first engaged portions 16, 17 and the second engaged portions 21, 22 of the arm member 11 are located in the pressing tube 31 at the distal side more than the engaging portion 32.

Figure 8:
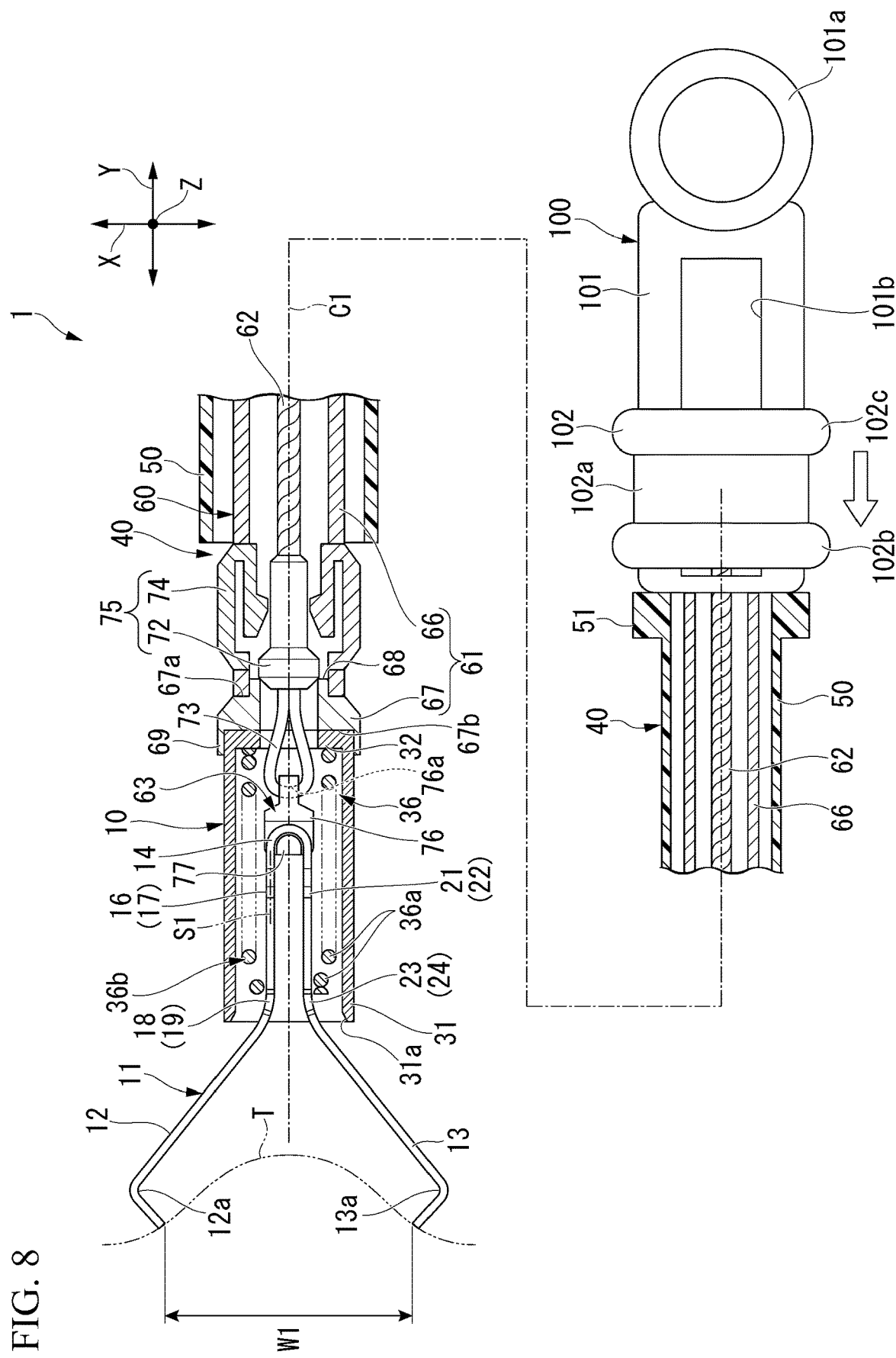
FIG. 8 is a partial cross-sectional view showing a state in which the restriction portion of the endoscope clip according to the present embodiment moves to the most distal end.
Figure 9:
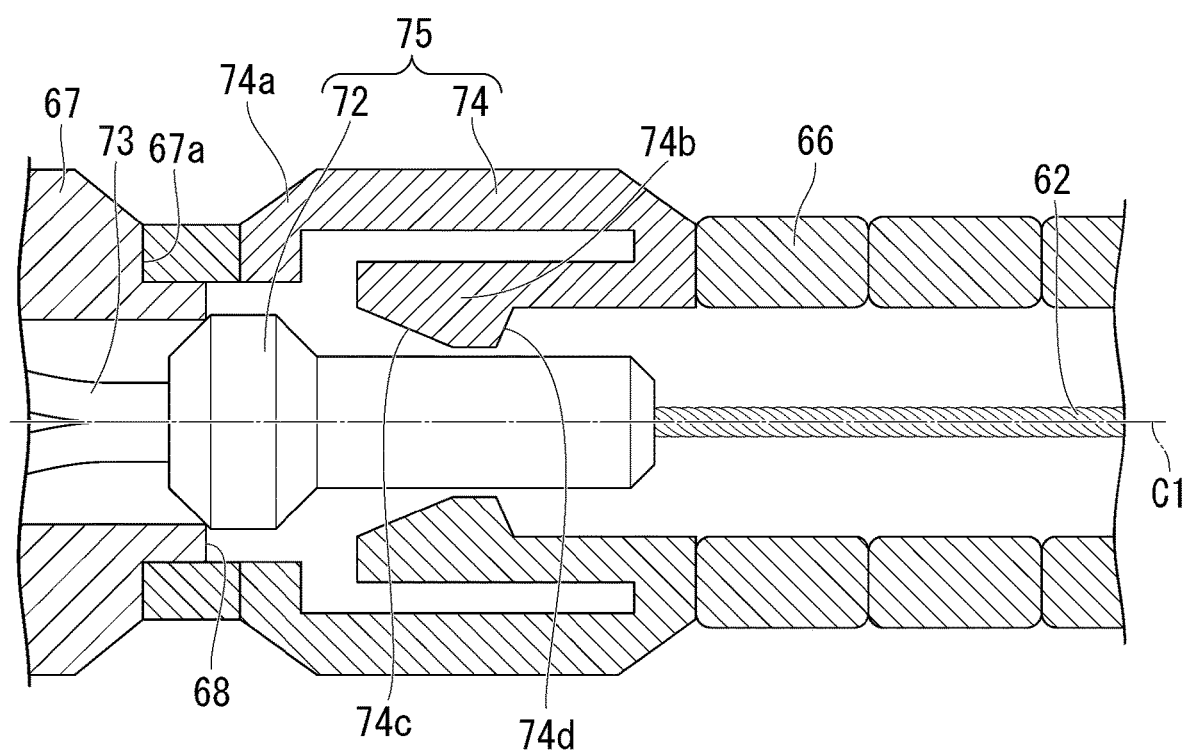
FIG. 9 is an enlarged cross-sectional view showing a state of the restriction portion of the endoscope clip in FIG. 8.

By the operator pushing the slider 102, as shown in FIGS. 8 and 9, the operation wire 62 may be advanced until the stopper 72 contacts the step portion 68 of the distal member 67. When the operation wire 62 advances, the arm member 11 advances together with the operation wire 62. Therefore, the opening width between the first arm 12 and the second arm 13 of the arm member 11 may increase while contacting the tapered surface 31*a* of the distal end portion of the pressing tube 31. For convenience of description, according to the present embodiment, a case in which the opening width of the arm member 11 continues to increase as the operation wire 62 advances will be described. In other words, when the stopper 72 comes into contact with the stepped portion 68 of the distal member 67 due to the advancement of the operation wire 62, the opening width of the arm member 11 becomes the maximum value W1. In this state, even if the operator does not grasp the slider 102, the stopper 72 engages with the step portion 68 of the distal member 67 and cannot move further toward the distal end side such that the state in which the opening width of the arm member 11 is becomes the maximum value W1 may be maintained.

However, the present disclosure is not limited thereto. For example, depending on the curved shape of the sheath in the meandering state, the opening width of the arm member 11 may reach the maximum value W1 before the stopper 72 abuts on and engages with the step portion 68 during the process in which the arm member 11 advances together with the operation wire 62. Even in this case, the first arm 12 and the second arm 13 of the arm member 11 may be suitably opened.

Subsequently, the operator may operate the endoscope (not shown) to adjust the orientation and posture of the arm member 11 of the clip 10 and press the arm member 11 toward the target tissue T.

According to the present embodiment, in the operation process of releasing the restriction by the restriction portion 75 of the endoscope clip 1, the operator may pull back the slider 102 toward the proximal end side such that the stopper 72 moves to the position to come into contact with the fixing member 74 again. At this time, the movement of the operation wire 62 toward the distal end side is restricted by the restriction portion 75, and the arm member 11 is transitioned from the open configuration to the closed configuration.

(Restriction State of the Endoscope Clip 1)

As shown in FIG. 8, the operator may position the target tissue T between the first arm 12 and the second arm 13 of the open configuration arm member 11 having the maximum opening width W1. When the operator confirms that the target tissue T is located between the first arm 12 and the second arm 13, the operator operates the endoscope to push the arm member 11 toward the target tissue T to grasp the target tissue T.

When the operator confirms that the target tissue T is located between the first arm 12 and the second arm 13, the operator grasps the operation portion main body 101 and pulls back the slider 102. At this time, the first arm 12 and the second arm 13 are moved toward the proximal end side together with the operation wire 62. In such a state, the first arm 12 and the second arm 13 come into contact with the tapered surface 31*a* (inner circumferential surface) of the distal end portion of the pressing tube 31, the first arm 12 is elastically deformed toward the second arm 13 side, and the second arm 13 is elastically deformed toward the first arm 12 side. As a result, the distal end of the first arm 12 and the distal end of the second arm 13 approach each other, and the opening width of the arm member 11 decreases. That is, in the state in which the target tissue T is positioned between the first arm 12 and the second arm 13, the arm member 11 is transitioned from the open configuration to the closed configuration. As a result, the target tissue T is grasped by the first arm 12 and the second arm 13. According to the present embodiment, a state in which a root of the target tissue T is tightly bound by the first arm 12 and the second arm 13 and the distance between the first arm 12 and the second arm 13 is approximately zero is also included in the closed configuration of the arm member 11. At this time, the elastic member 36 is compressed in the axial direction Y.

The operator pulls the slider 102 back to the proximal end side to move both the operation wire 62 and the stopper 72 to the proximal end side. The stopper 72 can again contact (engage) with the fixing member 74. As described above, since the stopper 72 has the tapered proximal end surface, it can easily get over the fixing member 74 while moving to the proximal end side.

Figure 10:
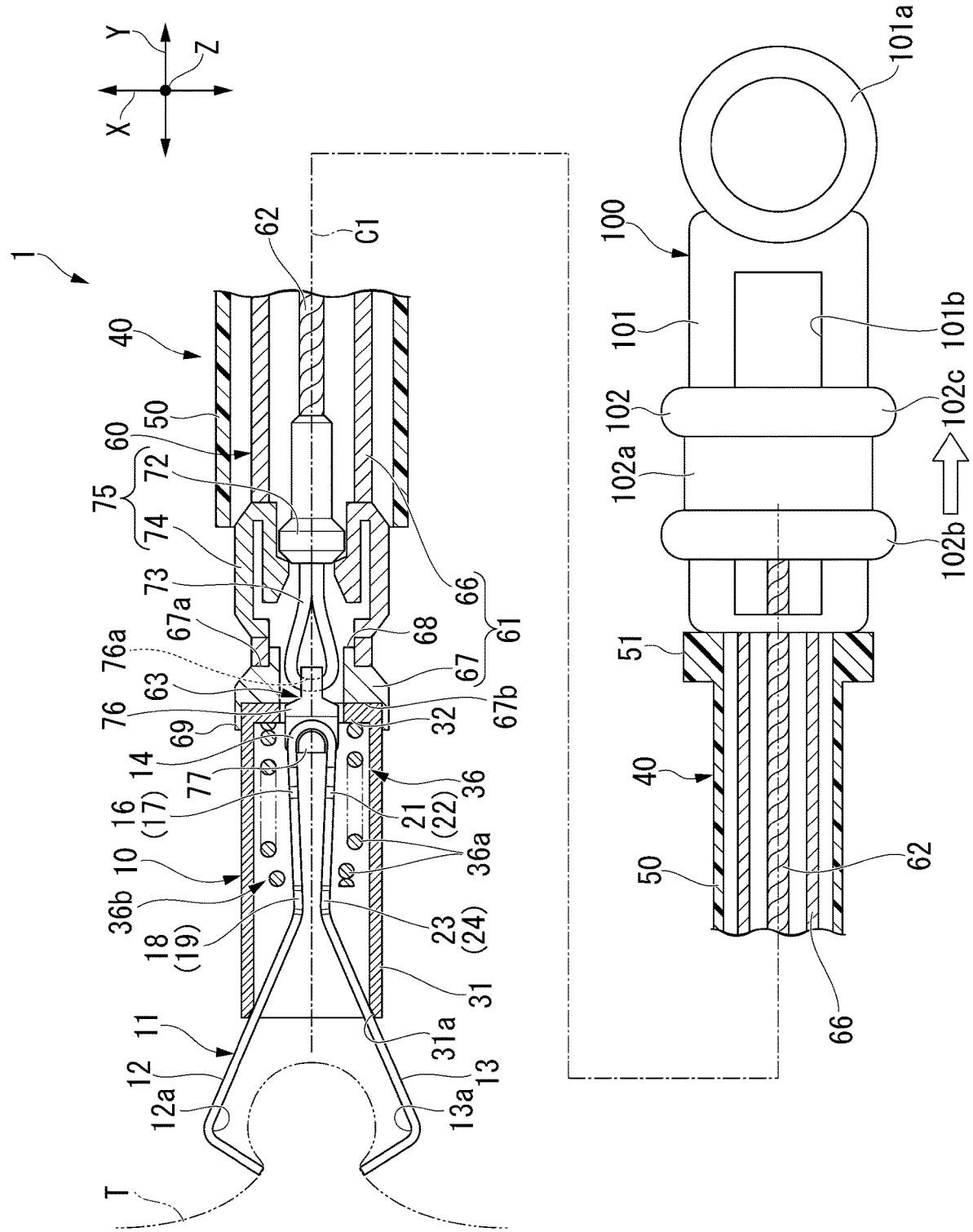
FIG. 10 is a partial cross-sectional view showing a state in which the endoscope clip according to the present embodiment grasps the target tissues.

As shown in FIG. 10, when the operator pulls back the slider 102 to the proximal end side, the stopper 72 enters a state in which the stopper 72 climbs on and overcomes the fixing member 74 to be positioned at the proximal end side more than the fixing member 74. In this state, the stopper 72 and the fixing member 74 are abutting (engaging with) each other. That is, in the natural state in which no external force applies, the restriction portion 75 may restrict the movement of the operation wire 62 toward the distal end side by the engagement of the stopper 72 and the fixing member 74.

In this state, the root of the target tissue T is tightly bound by the first arm 12 and the second arm 13 of the arm member 11 in the closed configuration. As described above, according to the present embodiment, the engagement of the stopper 72 and the fixing member 74 restricts the transition of the arm member 11 from the closed configuration to the open configuration. Therefore, even if the operator does not grasp the slider 102, the state in which the target tissue T is grasped by the arm member 11 in the closed configuration is maintained.

(Engaged State of Endoscope Clip 1)

Figure 11A:
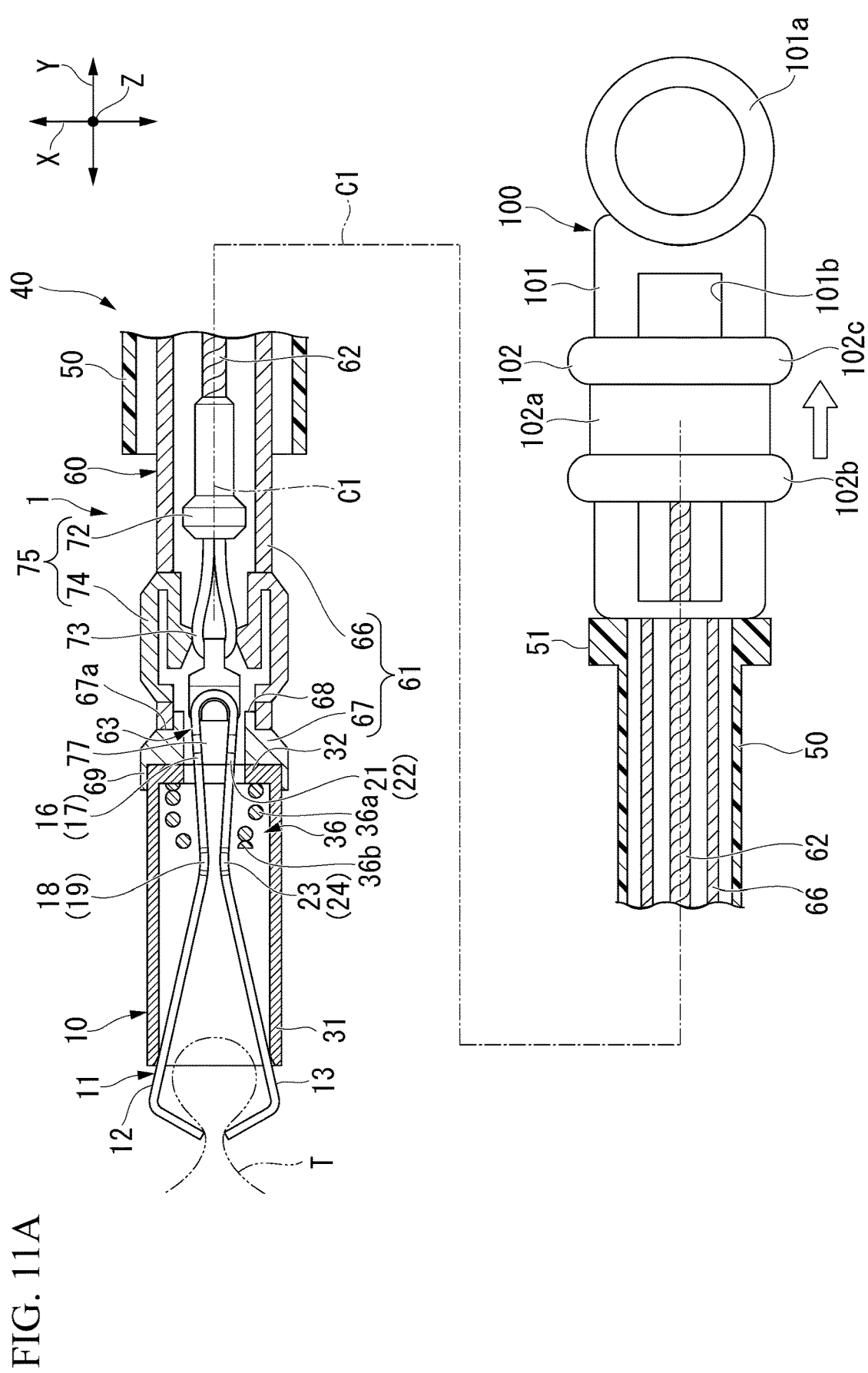
FIG. 11A is a partial cross-sectional side view showing a state of locking an arm member of the endoscope clip according to the present embodiment.
Figure 11B:
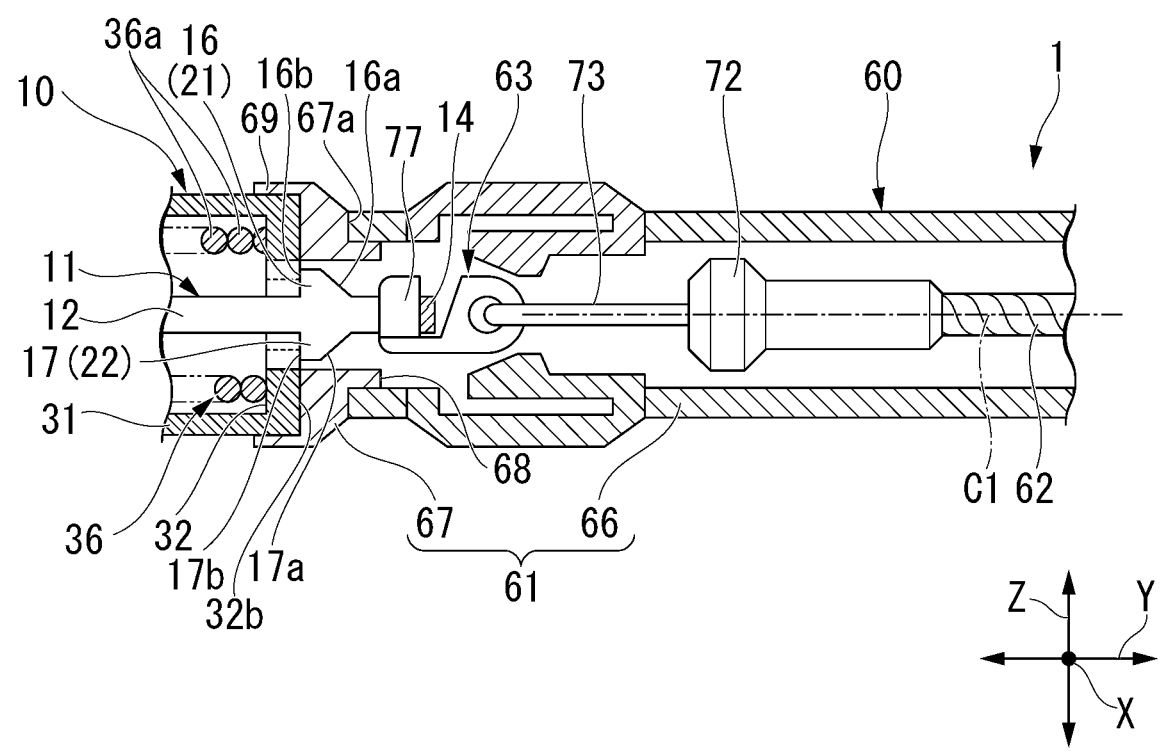
FIG. 11B is a partial cross-sectional planar view showing a distal end side of the endoscope clip in FIG. 11A.

In the state in which the target tissue T is grasped by the arm member 11 in the closed configuration, the operator may confirm the target tissue T using the endoscope. If it is confirmed that the target tissue T is grasped in a desired state by the arm member 11 of the clip 10, the operator proceeds to an operation of locking the grasping state of the clip 10 of the endoscope clip 1. More specifically, the first engaged portions 16, 17 and the second engaged portions 21, 22 of the arm member 11 are moved to climb on and overcome the engaging portion 32 of the pressing tube 31 to a position at the proximal end side more than the engaging portion 32. As a result, as shown in FIGS. 11A and 11B, both the distal end surface 16b of the first engaged portion 16 and the distal end surface 17b of the first engaged portion 17 contact the proximal end surface 32b of the engaging portion 32, and the first engaged portion 16 and the first locked portion 17 are engaged with the engaging portion 32. Similarly, both the distal end surface (not shown) of the second engaged portion 21 and the distal end surface (not shown) of the second engaged portion 22 contact the proximal end surface 32b of the engaging portion 32, and the second engaged portion 21 and the second engaged portion 22 are engaged to the engaging portion 32.

Hereinafter, an example of a process in which the first engaged portion 16 and the first engaged portion 17 are engaged by the engaging portion 32 will be described.

Firstly, when the operator grasps the operation portion main body 101 and pulls back the slider 102, the proximal end surface 16a of the first engaged portion 16 and the proximal end surface 17a of the first engaged portion 17 of the arm member 11, the proximal end surface (not shown) of the second engaged portion 21, and the proximal end surface (not shown) of the second engaged portion 22 are in contact with the engaging portion 32 of the pressing tube 31 to enter a contact state.

In the process of pulling back the slider 102, the elastic member 36 is compressed in the axial direction Y by the protrusion 18 and the protrusion 19. In this process, if the distance by which the slider 102 is pulled back toward the proximal end side increases, the degree of compression of the elastic member 36 also increases, such that the force necessary for the operator to pull back the slider 102 gradually increases. At the same time, the protrusions 18, 19, 23, 24 of the arm member 11 are moved to the proximal end side.

Since the connection member 63 of the treatment tool main body 40 is arranged in the pressing tube 31 or the sheath 61, the connection member 63 cannot rotate with respect to the loop portion 73, and the engagement of the hook 77 and the central portion 14 are maintained. As shown in FIGS. 11A and 11B, in this state, both the operation wire 62 and the stopper 72 are moved to the proximal end side. As a result, the engagement state between the stopper 72 and the fixing member 74 is released, and the stopper 72 is moved to a position separated from the fixing member 74 on the proximal end side more than the fixing member 74.

During the process of pulling back the slider 102 to the contact state, when the operator pushes the slider 102 toward the distal end side, the compressed elastic member 36 expands. The arm member 11 may move toward the distal end side with respect to the pressing tube 31 in a state in which the pressing tube 31 is in contact with the distal end support surface 67b of the distal end member 67. That is, in the process in which the slider 102 is pulled back, the operator may operate the endoscope so as to direct the clip 10 toward the target tissue T again. Subsequently, following the above-described procedures, it is possible to grasp the target tissue T again.

When the operator further pulls back the slider 102 from the above-mentioned contact state, the first arm 12 and the second arm 13 of the arm member 11 are further moved to the proximal end side together with the operation wire 62. At that time, the first arm 12 and the second arm 13 are elastically deformed in a direction of approaching each other and pass through the engaging portion 32.

In the process in which the operator pulls back the slider 102 to the proximal end side to reach the state in which the first engaged portions 16, 17 and the second engaged portions 21, 22 climb on and overcome the engaging portion 32, similarly to the above description, when the operator pushes the slider 102 toward the distal end side, the arm member 11 may be moved toward the distal end side. Accordingly, the arm member 11 may be transitioned from the closed configuration to the open configuration again. That is, the target tissue T may be grasped again until the arm member 11 reaches an overriding state.

In the process in which the operator pulls the slider 102 back toward the proximal end side and the first engaged portions 16, 17 climbs on and overcomes the engaging portion 32, compared with the process from the above-described initial state to the contact state, an increase rate of the necessary force for the operator to pulling the slider 102 per unit movement amount increases. That is, the operator feels heavy when pulling back the slider 102 from the contact state to the override state. Accordingly, the operator may recognize a state in which the slider 102 is currently pulled back.

In the process in which the operator pulls back the slider 102 to the proximal end side and the arm member 11 is changed from the contact state to the override state, the connection member 63 is arranged inside the sheath 61 such that the engagement of the hook 77 and the central portion 14 is maintained. The necessary amount of force for changing the arm member 11 from the contact state to the override state is about 20 to 50 N (Newton), for example.

When the first engaged portions 16, 17 and the second engaged portions 21, 22 move to the proximal end side beyond the engaging portion 32, the first engaged portions 16, 17 and the second locked portion may climb on and overcome the engaging portion 32 by scraping the engaging portion 32 or cause the engaging portion 32 to be deformed. In such a case, in order to prevent the excessive destruction to the engaging portion 32, it is preferable to perform chamfering process to the portion of the first engaged portions 16, 17 and the second engaged portions 21, 22 contacting with the engaging portion 32.

When the operator further pulls back the slider 102 from the above-mentioned override state, the first engaged portions 16, 17 and the second engaged portions 21, 22 move beyond the engaging portion 32 and further move toward the proximal end side. Both the configuration of the first arm 12 at the distal end side of the first engaged portions 16, 17 and the configuration of the second arm 13 at the distal side of the second engaged portions 21, 22 sequentially pass through the engaging portion 32. In the process, the positions of the first arm 12 and the second arm 13 in the opposite direction X and the orthogonal direction Z with respect to the pressing tube 31 are maintained. At this time, the first arm 12, the second arm 13, and the central portion 14 are not biased by the engaging portion 32. Accordingly, due to the elastic force of the central portion 14, the proximal end side of the first arm 12 and the proximal end side of the second arm 13 move in the opposite direction X to be separated from each other.

When the operating force for moving the arm member 11 to the proximal end side of the pressing tube 31 is released, the distal end surfaces 16b, 17b of the first engaged portions 16, 17 are in a state of being in contact with the proximal end surface 32b of the engaging portion 32.

In the process when the operator pulls back the slider 102 from the above-described override state to the engagement state, the first arm 12, the second arm 13, and the central portion 14 are no longer engaged by the engaging portion 32, and the elastically deformation in these configurations are partially released. Accordingly, in the process from the override state to the engagement state, the necessary amount of force for the operator to pull back the slider 102 gradually decreases.

In the process when the operator pulls back the slider 102 from the above-described override state to the engagement state, the clip 10 is maintained in the closed configuration. Since the connection member 63 is arranged inside the sheath 61, the engagement between the hook 77 and the central portion 14 is maintained.

As shown in FIGS. 11A, 11B, when the clip 10 is in the engagement state, the strand 36a of the elastic member 36 that is compressed in the axial direction Y enters a close winding state in which the strands 36a adjacent to each other in the axial direction Y are in almost close contact with each other. When the clip 10 is in the engagement state, the distal end surfaces 16b, 17b of the first engaged portions 16, 17 are engaged to the proximal end surface 32b of the engaging portion 32 such that the movement of the arm member 11 toward the distal end side of the arm member 11 with respect to the pressing tube 31 is restricted. That is, the state in which the clip 10 ligates the target tissue T is maintained.

In this state, the stopper 72 is positioned at a position apart from the fixing member 74 and at the proximal end side more than the fixing member 74. In this state, in the clip 10, the engaging force generated when the first engaged portions 16, 17 are engaged to the proximal end surface 32b of the engaging portion 32 and the elastic force of the elastic member 36 are in balance. Accordingly, the support portion 69 formed at the distal end side of the distal member 67 does not support the outer circumferential surface of the pressing tube 31 in contact with the distal end support surface 67b.

As a result, when the operator pushes the slider 102, the operation wire 62, the connection member 63, and the clip 10 may be moved to the distal end side.

(Release State of Endoscope Clip 1)

Subsequently, the operator separates the clip 10 ligating the target tissue T from the treatment tool main body 40. More specifically, when the operator pushes the slider 102, the operation wire 62, the connection member 63, and the clip 10 move toward the distal end side with respect to the coil sheath 66.

Figure 12:
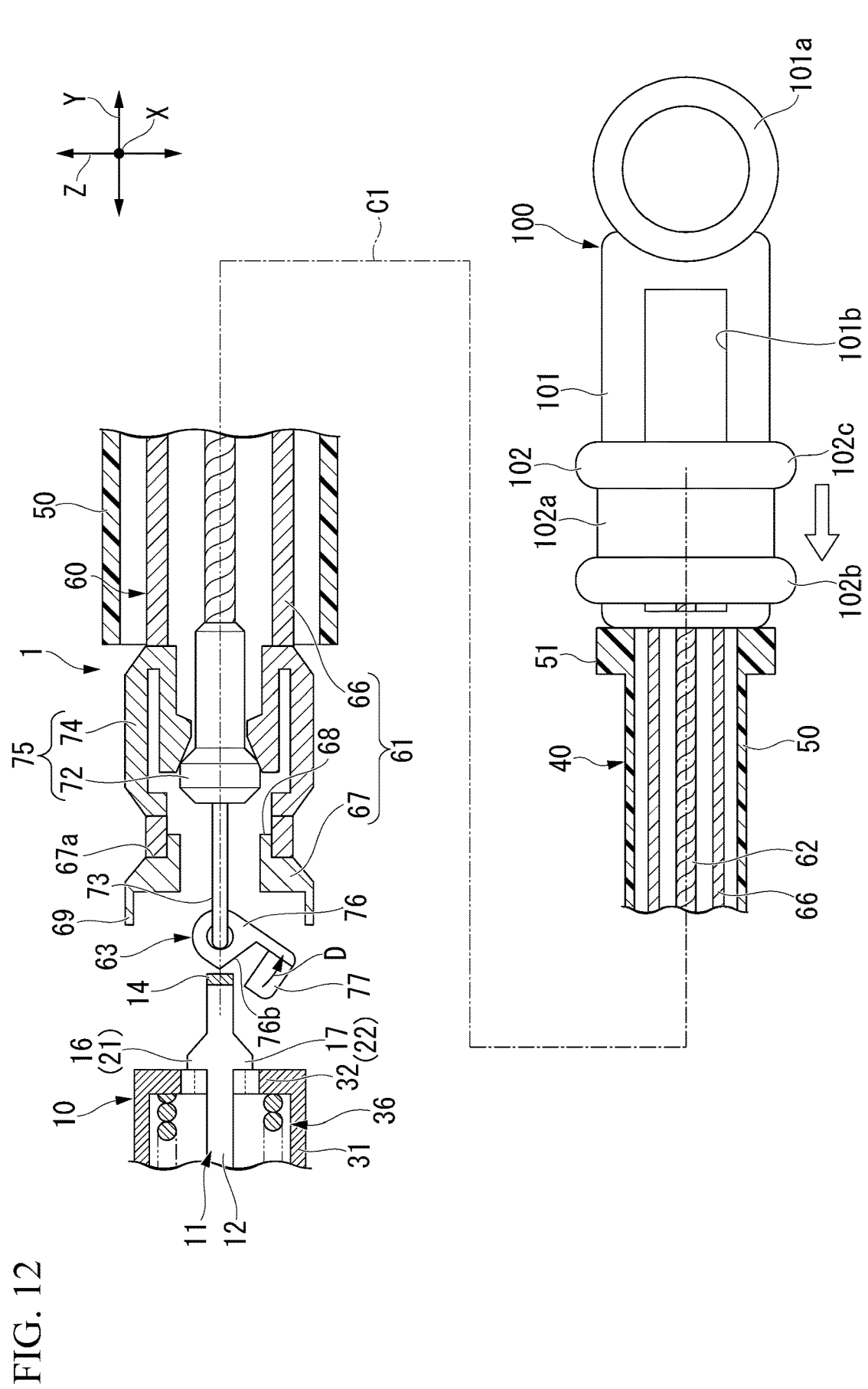
FIG. 12 is a partial cross-sectional view showing an operation of indwelling a clip unit of the endoscope clip according to the present embodiment in the body.

As shown in FIG. 12, when the connection member 63 projects toward the distal side more than the distal member 67, the arm member 11 and the pressing tube 31 move integrally toward the distal end side. When the connection member 63 is located outside the pressing tube 31 by the operator pushing the slider 102, the connection member 63 may rotate with respect to the loop portion 73. When the operator pushes the slider 102 and moves the operation wire 62 toward the distal end side, the inclined surface 76b of the connection member 63 comes into contact with the proximal end surface of the central portion 14 of the clip 10 that ligates the target tissue T. As shown in FIG. 12, the hook 77 rotates in the direction D together with the connecting portion main body 76 by being guided by the inclined surface 76b, and the engagement between the hook 77 and the central portion 14 is released. At this time, the clip 10 maintains the closed configuration.

As a result, the clip 10 ligating the target tissue T is indwelled in the body.

After the clip 10 ligating the target tissue T is indwelled in the body, the operator pulls back the slider 102 to accommodate the connection member 63 in the sheath 61. Subsequently, the operator pulls out and removes the endoscope clip 1 from the channel of the endoscope. Finally, the operator takes necessary measures and ends the series of procedures.

(Effect of the Endoscope Clip 1)

Hereinafter, the effect of the endoscope clip 1 according to this embodiment will be described.

The arm member 11 of the clip 10 according to the present embodiment has the first arm 12 and the second arm 13. The arm member 11 has the closed configuration in which the first arm 12 and the second arm 13 are closed, and the open configuration in which the first arm 12 and the second arm 13 are spaced apart from each other. In the sheath 61 of the endoscope clip 1 according to the present embodiment, a restriction portion 75 having the stopper 72 that moves together with the operation wire 62, and the fixing member 74 in which the inner cavity with the width smaller than the outer diameter of the stopper 72 is formed. The restriction portion 75 may restrict the movement of the operating wire 62 toward the distal end side by the stopper 72 and the fixing member 74 engaging with each other. Accordingly, when the target tissue T in the body is treated and the stopper 72 is located at the proximal end side more than the fixing member 74, the operator does not have to operate the slider 102 of the operation unit 100 disposed at the proximal end side and the movement of the wire 62 toward the distal end side is restricted. Accordingly, the transition of the arm member 11 from the closed configuration to the open configuration may be restricted.

As a result, according to the endoscope clip 1 according to the present embodiment, when the target tissue T in the body is treated, it is easy to maintain the closed configuration of the arm member 11, and the unintentional contact of the arm member 11 to the inner wall of the channel of the endoscope or the tissues inside of the body may be prevented. Since the operator can shorten the operation of adjusting the endoscope clip 1, it is possible to facilitate the handling, save the operation time, and improve the efficiency.

According to the endoscope clip 1 according to the present embodiment, in the state in which the stopper 72 of the restriction portion 75 and the fixing member 74 are engaged with each other, the restriction force by the restriction portion 75 and the elastic force of elastic member 36 disposed in the pressing tube 31 are in balance. Accordingly, it is not necessary for the operator to apply an operating force amount equal to or larger than the elastic force of the elastic member 36 in order to release the restriction of the movement of the operation wire 62 toward the distal end side by the restriction portion 75, and the restriction by the restriction portion 75 may be released by a slight force. According to the endoscope clip 1 according to the present embodiment, the restriction portion 75 is provided in the sheath 61 in a region close to the distal end side.

According to the configuration of the endoscope clip 1 according to the present embodiment, even when the endoscope clip 1 is inserted into a luminous cavity having a complicated shape and the coil sheath 66 is meandering, it is possible to suppress the change in the path length between the stopper 72 and the arm member 11. As a result, the arm member 11 may be further reliably maintained in the closed configuration by the engagement of the fixing member 74 and the stopper 72.

According to the endoscope clip 1 according to the present embodiment, the restriction portion 75 has a simple configuration including the stopper 72 and the fixing member 74, and the manufacturing thereof is easy. Accordingly, the endoscope clip 1 may be manufactured at low cost.

In the present embodiment, with respect to the configuration of the restriction portion 75 of the endoscope clip 1, an example of the fixing member 74 having the supporting portion 74a and the deforming portion 74b has been described; however, the configuration of the restriction portion 75 is not limited thereto. According to the present embodiment, the restriction portion only has to be capable of restricting the movement of the operation wire 62 toward the distal end side even when the operator does not grasp the slider 102, and the specific configuration is not particularly limited.

(Modification)

Hereinafter, the configuration of an endoscope clip according to a modification of the present embodiment will be described with reference to FIGS. 13 to 15. Hereinafter, the description of the same configuration as the endoscope clip 1 according to the above-described embodiment will be omitted, and the description will focus on the points different from the above-described embodiment.

Figure 13:
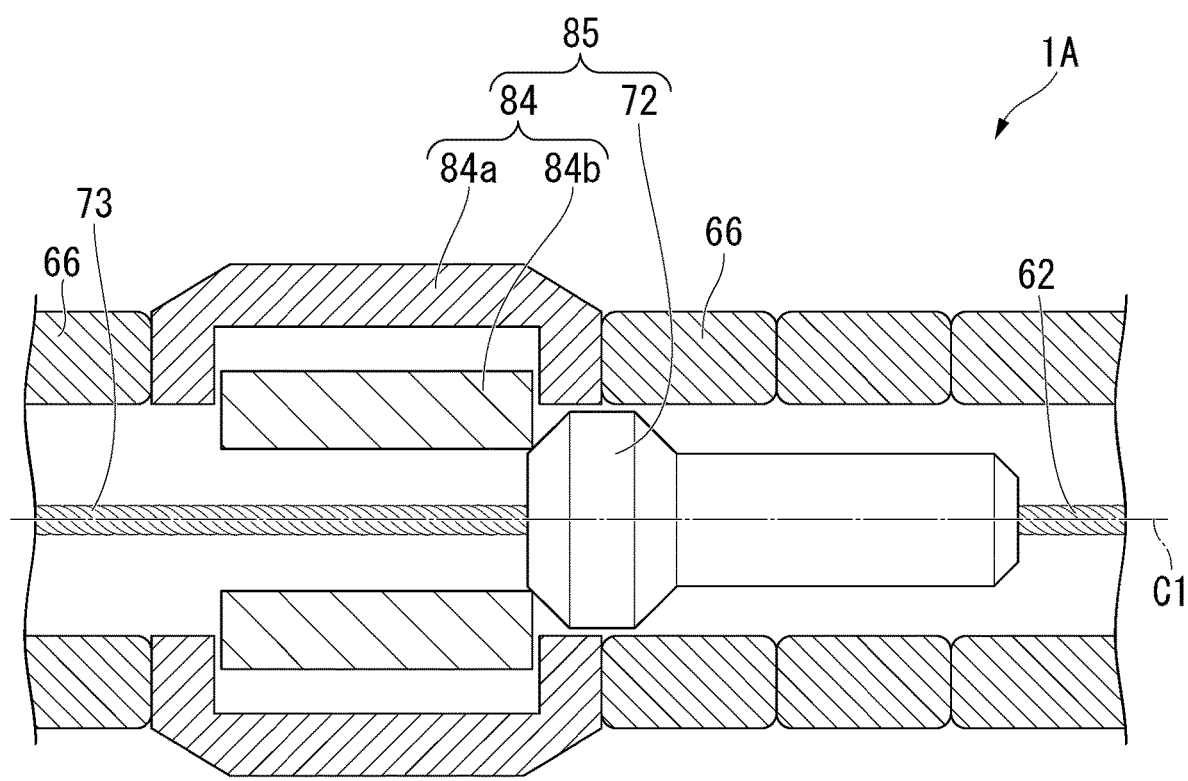
FIG. 13 is an enlarged cross-sectional view showing a configuration of a restriction portion according to a modification example according to the present embodiment.

FIG. 13 is an enlarged cross-sectional view showing a configuration of part of the endoscope clip 1 according to the present modification. FIG. 14 is an enlarged cross-sectional view showing a state in which the restriction by a restriction portion 85 of the endoscope clip 1 according to the present modification is released. FIG. 15 is a perspective view showing the configuration of the engaged member 84b of the restriction portion 85 according to the present modification.

The endoscope clip 1 according to the present modification is configured to include the restriction portion 85 instead of the restriction portion 75 included in the endoscope clip 1 according to the above-described embodiment. As shown in FIG. 13, the restriction portion 85 of the endoscope clip 1 according to the present modification is configured to have an engaged portion 84 and a stopper (engaging portion) 72.

As shown in FIG. 13, the engaged portion 84 of the endoscope clip 1 according to the present modification includes a support member 84a and a C-shaped ring member (deformation portion) 84b. A distal end and a proximal end of the support member 84a are connected to the strands configuring the coil sheath 66 and the support member 84a is configured integrally with the coil sheath 66. In the present modification, the support member 84a may be integrally configured with the coil sheath 66 by a method such as welding or the like.

As shown in FIG. 13, in the present modification, the support member 84a is not limited to the example in which the support member 84a is sandwiched by the strands forming the coil sheath 66. For example, the support member 84a may be arranged at the distal end side more than the coil-sheath 66, and the proximal end of the support member 84 along the axial direction Y may be fixed to the strands configuring the coil sheath 66 by a method such as welding, bonding or the like.

As shown in FIG. 13, the support member 84a of the engaged portion 84 may have an outer diameter in the radial direction with respect to the axis C1 that is slightly larger than the outer diameter of the coil sheath 66. The support member 84a is formed in a pipe shape, and has an inner cavity to be capable of accommodating the ring member 84b therein.

Figure 15:
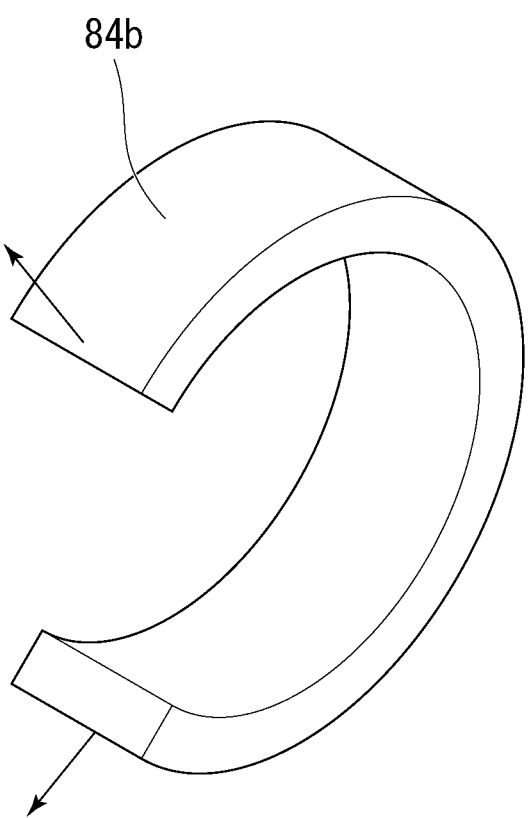
FIG. 15 is a perspective view showing a configuration of an engaged member of the restriction portion according to the present modification example.

As shown in FIG. 15, the ring member 84b is formed in a C shape, however, the ring member 84 b is not limited only to the configuration. According to the present modification, the ring member 84b may be formed by cutting out a part of a tubular member, for example.

As shown in FIG. 13, in the natural state in which no external force applies, a space having a width smaller than the outer diameter of the stopper 72 is formed inside the ring member 84b. As shown in FIG. 15, when an external force is applied, the ring member 84b can expand and be elastically deformed in the direction indicated by the arrow.

As shown in FIG. 13, the ring member 84b has an outer diameter that is the maximum width in the radial direction with respect to the axis C1 to be equal to or larger than the inner diameters of the support member 84a at the distal end portion and the proximal end portion thereof, and the outer diameter of the ring member 84b is equal to or less than the inner diameter of the inner cavity of the support member 84a. That is, in the present modification, the engaged portion 84 is configured that the support member 84a and the ring member 84b are combined such that the ring member 84b is rotatable in the inner cavity of the support member 84a and the ring member 84b does not fall out from the inner cavity.

The material for configuring the engaged portion 84 of the endoscope clip 1 according to the present modification is not particularly limited. For example, in order to ensure durability, the engaged portion 84 may be formed of the same metal material as the pressing tube 31 and the engaging portion 32.

Other configurations of the endoscope clip 1 according to the present modification may be the same as those of the endoscope clip 1 according to the above embodiment.

As shown in FIG. 13, the endoscope clip 1 according to the present modification has the above-described configuration such that when the stopper 72 is positioned at the proximal end side more than the engaged portion 84, the stopper 72 is biased toward the distal end side due to the elastic force of the elastic member 36 and in contact (engaged with) to the ring member 84b of the engaged member 84. In this state, the elastic force of the elastic member 36 and restriction force opposite to the elastic force of the elastic portion 36 and generated by the contact between the stopper 72 and the ring member 84b are in balance. Accordingly, the movement of the stopper 72 and the operation wire 62 connected to the stopper 72 toward the distal end side is restricted. According to the endoscope clip 1 of the present modification, in the natural state where no external force is applied, the stopper 72 and the ring member 84b are engaged with each other such that the transition of the arm member 11 from the closed configuration to the open configuration may be restricted.

Figure 14:
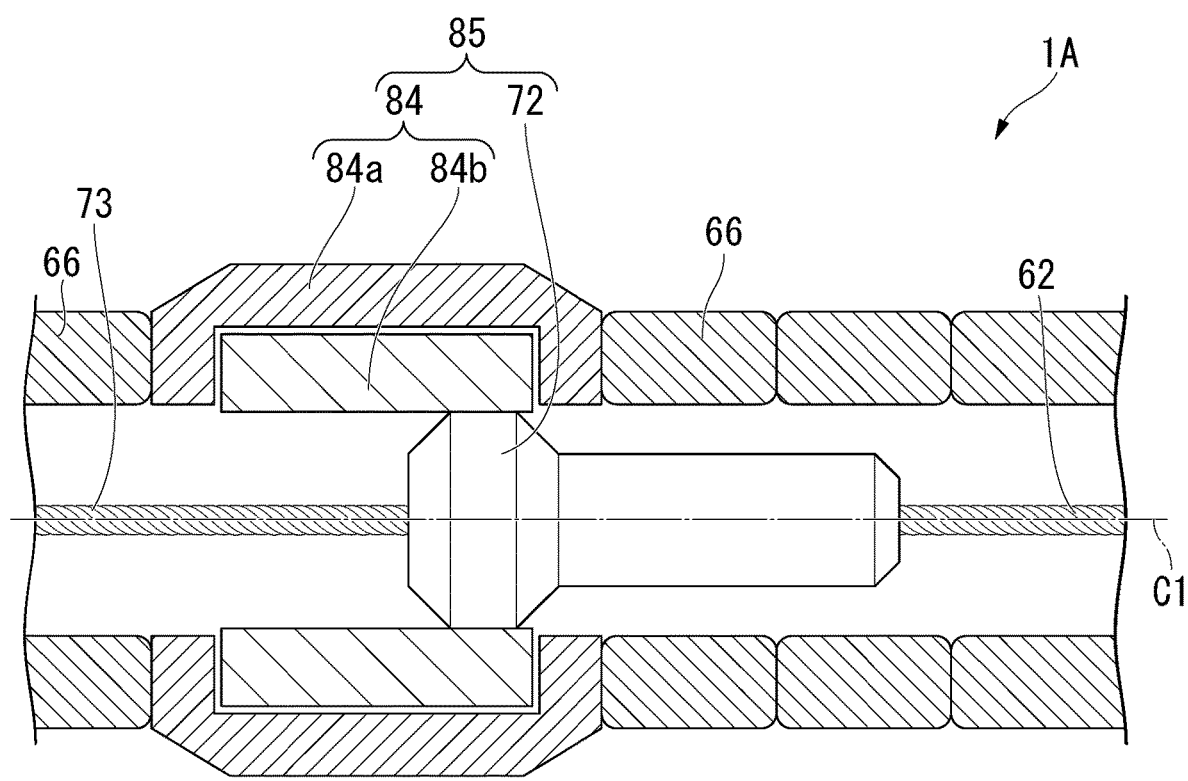
FIG. 14 is an enlarged cross-sectional view showing an operation of releasing the restriction due to the restriction portion of the endoscope clip according to the present modification example.

As shown in FIG. 14, when the sum of the operating force by the operator and the elastic force of the elastic member 36 exceeds the maximum value of the restriction force generated by the engagement of the stopper 72 of the restriction portion 85 and the engagement portion 84 by the operator pushing the slider 102, the ring member 84 is elastically deformed and the space formed inside the ring member 84 is expanded. Accordingly, the stopper 72 may pass through the space formed in the ring member 84b. In this state, when the operator pushes the slider 102, the stopper 72 moves toward the distal end side with respect to the ring member 84b while contacting the inner circumferential surface of the ring member 84b.

When the operator pushes the slider 102, the stopper 72 moves toward the distal end side with respect to the ring member 84b, and when the stopper 72 climbs on and overcomes the ring member 84, the restriction of the movement of the operation wire 62 toward the distal end side by the restriction portion 85 is released. That is, the restriction of the transition of the arm member 11 from the closed configuration to the open configuration by the restriction portion 85 is also released.

Subsequently, the operator may operate the slider 102 to treat the target tissue T as the same procedures by using the endoscope clip 1 according to the above-described embodiment.

According to the endoscope clip 1 of the present modification, similar to the above-described embodiment, the closed configuration of the arm member 11 may be easily maintained and contact with the inner wall of the channel of the endoscope or the tissue in the body may be prevented. Since the operator can shorten the operation of adjusting the endoscope clip 1, it is possible to facilitate the handling, save the operation time, and improve the efficiency.

Second Embodiment

In the above-described first embodiment and modification of the present disclosure, an example in which the restriction portion for restricting the movement of the operation wire toward the distal end side is formed in the sheath portion of the endoscope clip has been described. However, the endoscope clip according to the present disclosure is not limited thereto. The endoscope clip according to the present disclosure may have a configuration in which the restriction portion is provided in the operation portion at the proximal end side of the endoscope clip. That is, the endoscope clip according to the present disclosure may have a configuration in which the movement of the operation wire toward the distal side is restricted by restricting the movement of the slider of the operation portion toward the distal end side.

Hereinafter, in the endoscope clip of the present disclosure, a configuration in which the restriction portion is provided in the operation portion at the proximal end side will be described.

Hereinafter, a configuration of an endoscope clip 2 according to a second embodiment of the present disclosure will be described with reference to FIGS. 16A to 17B. In the description of the endoscope clip 2 according to the present embodiment, the description of the same configuration as the endoscope clip 1 according to the first embodiment described above will be omitted, and the points different from the first embodiment described above will be mainly described.

Figure 16A:
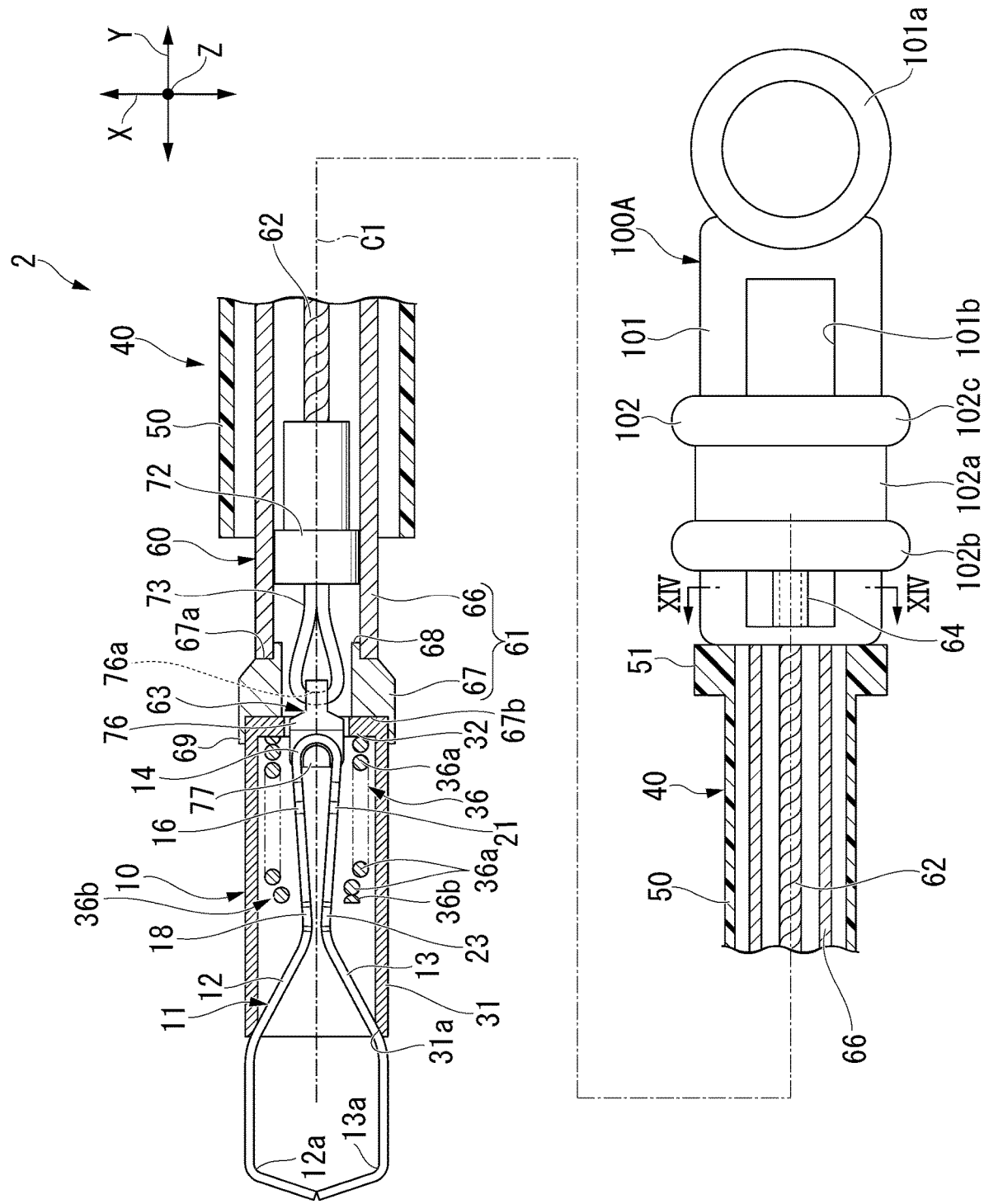
FIG. 16A is a partial cross-sectional side view schematically showing a configuration of an endoscope clip according to a second embodiment of the present disclosure.
Figure 16B:
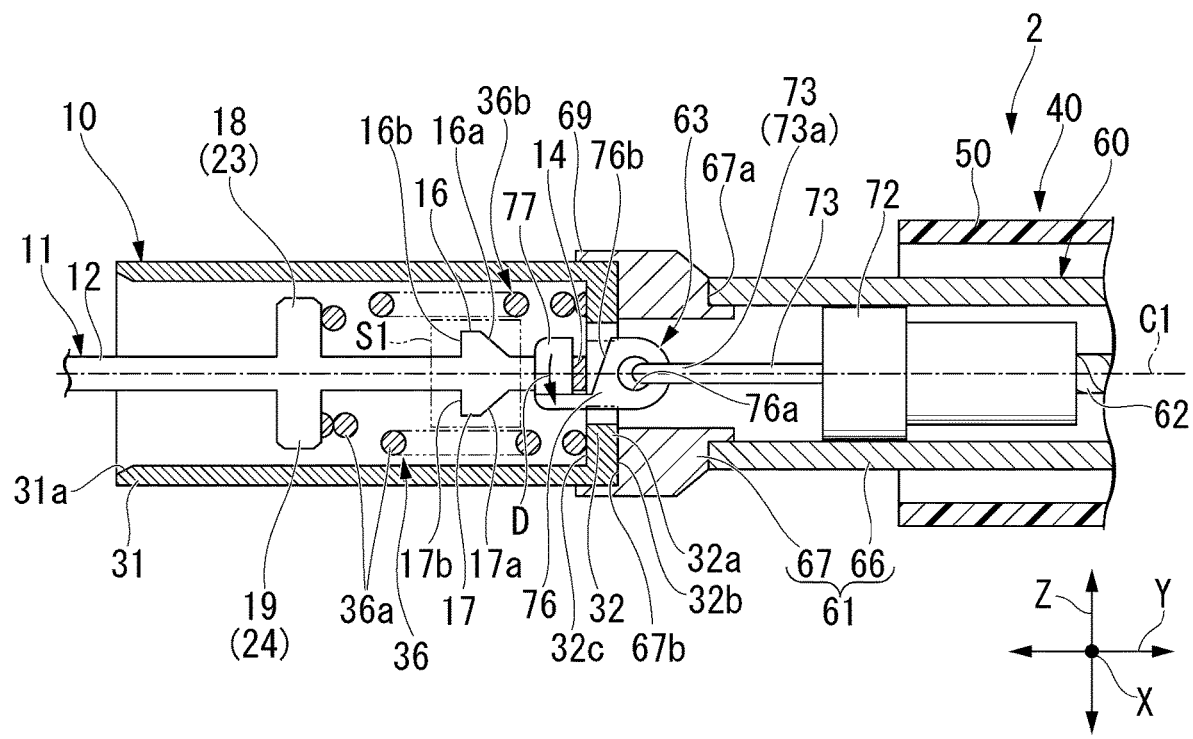
FIG. 16B is a partial cross-sectional planar view showing a distal end side of the endoscope clip in FIG. 16A.
Figure 16C:
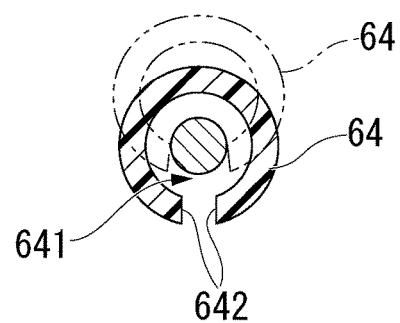
FIG. 16C is a cross-sectional view showing an operation portion of the endoscope clip in a radial direction in FIG. 16A.
Figure 17A:
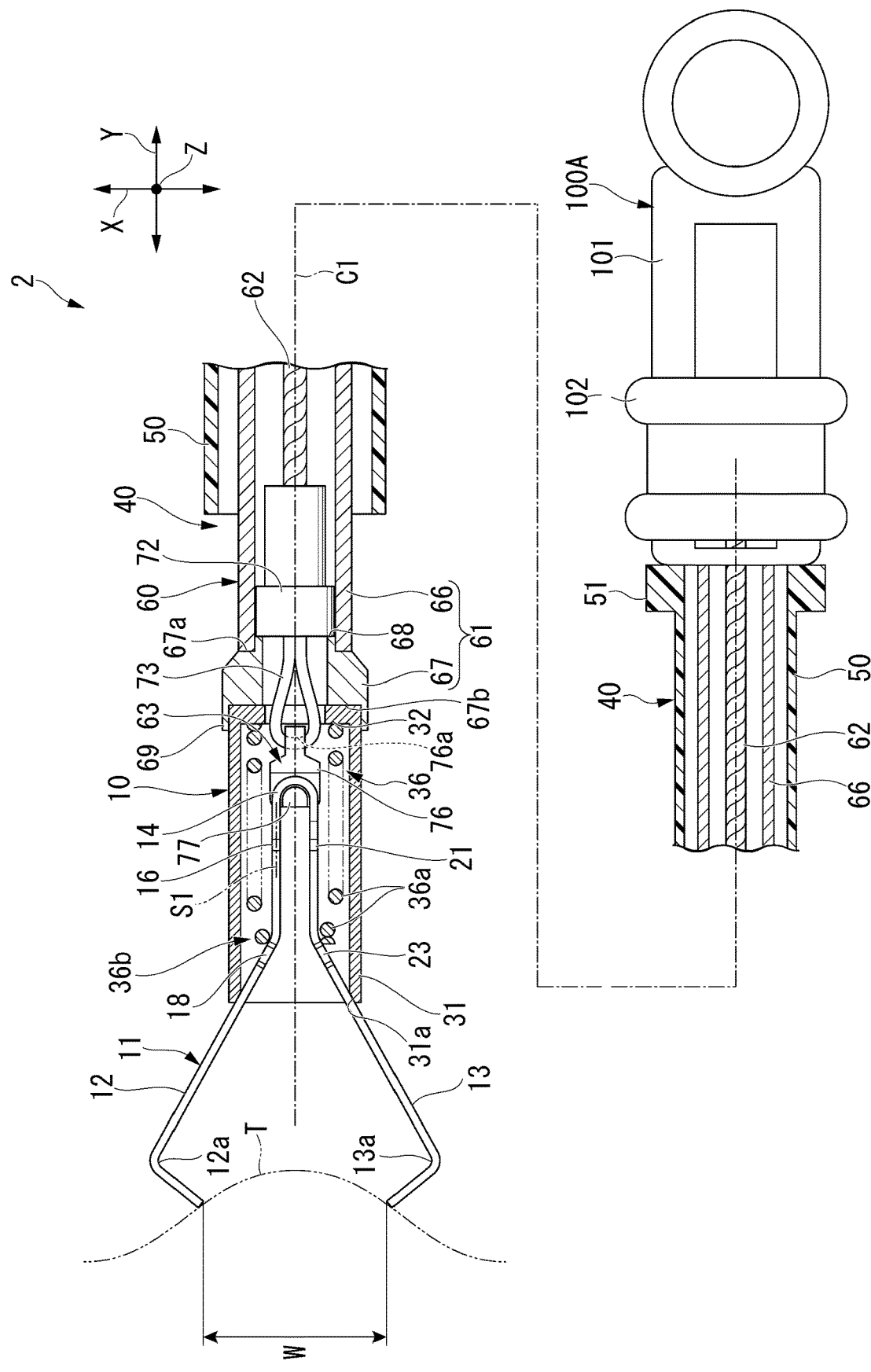
FIG. 17A is a partial cross-sectional view showing a state of releasing the restriction by the restriction portion of the endoscope clip according to the present embodiment.
Figure 17B:
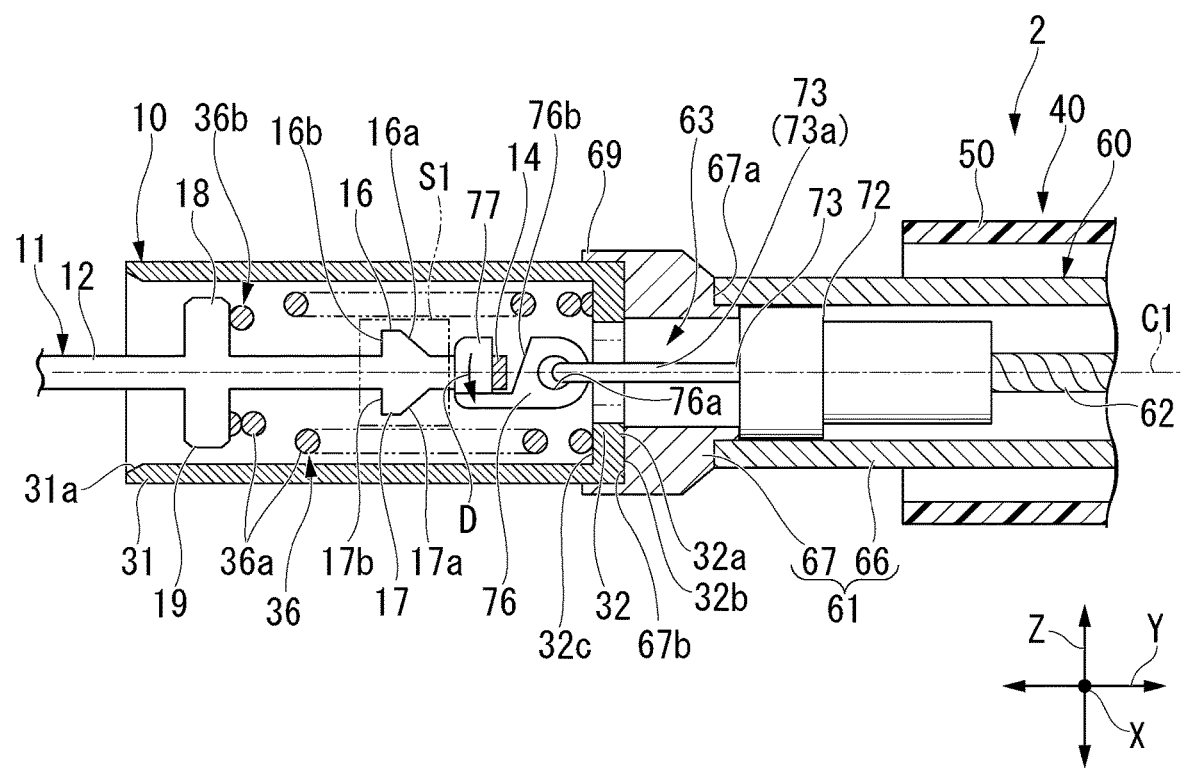
FIG. 17B is a partial cross-sectional planar view schematically showing a distal end side of the endoscope clip in FIG. 17A.

FIG. 16A is a partial cross-sectional side view showing a state in which movement of the operation wire 62 toward the distal end side is restricted by the fixing member in the endoscope clip 2 according to the present embodiment. FIG. 16B is a partial cross-sectional plan view schematically showing the distal end side of the endoscope clip in FIG. 16A. FIG. 16C is a radial cross-sectional view of the operation portion of the endoscope clip in FIG. 16A. FIG. 17A is a partial cross-sectional side view showing a state in which the restriction by the restriction portion of the endoscope clip 2 according to the present embodiment is released. FIG. 17B is a partial cross-sectional plan view schematically showing the distal end side of the endoscope clip in FIG. 17A.

As shown in FIG. 16A, the endoscope clip 2 according to the present embodiment is different from the endoscope clip 1 according to the first embodiment described above in that the endoscope clip 2 has a fixing member 64 disposed in the operation portion 100A at the proximal end side instead of the fixing member 74 disposed in the sheath 61 of the treatment tool main body 40.

As shown in FIG. 16A, the operation portion 100A of the endoscope clip 2 according to the present embodiment has the operation portion main body 101, the slider 102, and the fixing member 64. The fixing member 64 is a hollow tube-shaped member formed to extend along the axial direction Y of the slider 102. As shown in FIG. 16C, the fixing member 64 is formed with an inner cavity 641 into which the operation wire 62 can be inserted. The fixing member 64 can be formed of, for example, a resin material. The fixing member 64 has such a rigidity that it is not compressed even if a predetermined pressure in a longitudinal axis direction of itself is applied. More specifically, the fixing member 64 has a rigidity so as to not to be crushed by the elastic force of the elastic member 36 provided in the pressing tube 31.

The dimension of the fixing member 64 in the longitudinal axis direction is not particularly limited. For example, the dimension of the fixing member 64 in the longitudinal axis direction may be equal to or smaller than a value obtained by subtracting the dimension of the slider 102 in the longitudinal axis from the dimension of the slit 101b of the operation portion main body 101 in the longitudinal axis direction. However, since the dimension of the fixing member 64 in the longitudinal axis direction and the opening width of the arm member 11 have a correlation, it is preferable to determine the dimension of the fixing member 64 in the longitudinal axis direction in consideration of the desired opening width of the arm member 11. According to the present embodiment, for example, the dimension of the fixing member 64 in the longitudinal axis direction is preferably determined such that when the slider 102 is advanced to be in contact with the fixing member 64 in the slit 101b of the operation portion main body 101, the arm member 11 may be in the closed configuration.

As shown in FIG. 16C, in the radial cross-sectional view of the slider 102 along the axial direction C1, the fixing member 64 has a substantially C-shaped cross section. The fixing member 64 is formed with a slit portion 642 that connects the inner cavity 641 and the outside. The slit portion 642 is an elongated notch formed to extend along the axial direction C1. The slit portion 641 is formed with an opening width being slightly smaller than the diameter of the operation wire 62. As described below, when the operator removes the fixing member 64, the slit portion 641 may be deformed until a gap having a dimension through which the operation wire 62 may pass is formed.

As shown in FIG. 16B, the endoscope clip 2 according to the present embodiment is configured that the configuration of the clip 10, and the connection configuration of the clip 10 and the operation wire 62 are similar to the first embodiment. In the endoscope clip 2 according to the present embodiment, the insertion portion 60 includes the sheath 61, the operation wire 62, the connection member 63, and the loop portion 73. Different from the endoscope clip 1 according to the first embodiment, the endoscope clip 2 according to the present embodiment is configured such that the fixing member 64 in not disposed in the sheath 61.

Hereinafter, a procedure for ligating the target tissue T using the endoscope clip 2 according to the present embodiment will be described with reference to FIGS. 16A to 17B. In the following description, the point of restricting the movement range of the operation wire 62 by restricting the movement range of the slider 102 using the fixing member 64 will be focused. Other operations may be performed in the same manner as the procedure using the endoscope clip 1 according to the first embodiment described above, and thus the description thereof will be omitted.

As shown in FIG. 16A, in the operation portion 100A of the endoscope clip 2 according to the present embodiment, the fixing member 64 is arranged in the slit 101b of the operation portion main body 101 while covering the operation wire 62, and the fixing member 64 is in contact with the distal of the slit 101b. The fixing member 64 is arranged in the slit 101b at the distal end side more than the slider 102. That is, the distal end surface of the slider 102 is in contact with the fixing member 64 in the slit 101b of the operation portion main body 101.

At this time, the movable range of the slider 102 is a range by subtracting the dimension of the fixing member 64 in the longitudinal axis direction from the length of the slit 101b from the proximal end of the slit 101b of the operation portion main body 101 toward the distal end side. In other words, the fixing member 64 according to the present embodiment is a member configured to restrict a pushing amount (moving amount toward the distal end side) of the operation wire 62.

In the endoscope clip 2 according to the present embodiment, in the natural state in which the operator does not grasp the slider 102 of the operation unit 100A, that is, the external force does not apply, the elastic force of the elastic member 36 provided in the pressing tube 31 applies to the operation wire 62 to move the operation wire 62 toward the distal end side. In this state, the slider 102 contacts and presses the fixing member 64 toward the distal side along the direction of the axis C1.

The fixing member 64 of the endoscope clip 2 according to the present embodiment has the rigidity so as to not to be crushed by the elastic force of the elastic member 36. More specifically, the fixing member 64 has the rigidity so as to not to be elastically deformed or be elastically deformed without being plastically deformed when the slider 102 presses against the fixing member 64 due to the elastic force of the elastic member 36 applied on the operation wire 62.

As shown in FIG. 16A, when the fixing member 64 is arranged in the slit 101b of the operation unit 100A, the slider 102 cannot move further toward the distal side than the position where contacting on the fixing member 64. In other words, the endoscope clip 2 according to the present embodiment may restrict the movement of the operation wire 62 toward the distal end side by the slider 102 contacting the fixing member 64. It is considerable that the fixing member 64 of the endoscope clip 2 according to the present embodiment restricts the movement of the operation wire 62 toward the distal end side.

As shown in FIG. 16A, when the slider 102 contacts the fixing member 64, the arm member 11 is in the closed configuration. That is, the arm member 11 is in a state where the first arm 12 and the second arm 13 are in contact with each other, or in a state where the distance between the distal of the first arm 12 and the distal of the second arm 13 is substantially zero. A portion of each of the first arm 12 and the second arm 13 of the arm member 11 from the distal end to the proximal end thereof is in contact with the tapered surface 31 formed on the inner circumferential surface of the distal end portion of the pressing tube 31.

At this time, both the operation wire 62 connected to the slider 102 and the arm member 11 connected to the operation wire 62 are in a state in which they cannot be advanced with respect to the operation unit main body 101. As a result, as shown in FIG. 16A, the transition of the arm member 11 from the closed configuration to the open configuration is restricted, and the closed configuration of the arm member 11 is maintained.

Therefore, the fixing member 64 of the endoscope clip 2 according to the present embodiment may restrict the transition of the arm member 11 from the closed configuration to the open configuration.

As shown in FIGS. 17A to 17B, when the operator removes the fixing member 64, the movable range of the slider 102 is within the entire length of the slit 101b of the operation portion main body 101 in the longitudinal axis direction. That is, as shown in FIGS. 17A and 17B, when the operator removes the fixing member 64, by the operator pushing the slider 102, the operation wire 62 may be movable toward the distal end side until the stopper 72 contacts the step portion 68 of the distal member 67.

In the endoscope clip 2 according to the present embodiment, as the operation wire 62 moves toward the distal end side, in the arm member 11 of the clip 10, part of the first arm 12 and the second arm 13 is in contact with the tapered surface 31a of the pressing tube 31 the distal ends of the first arm and the second arm 13 are in the separated state. As the operator pushes in the slider 102, the first arm 12 and the second arm 13 of the arm member 11 are separated from each other such that the distance between the distal ends of the first arm 12 and the second arm 13 becomes large. That is, the operator may cause the arm member 11 to be transitioned from the closed configuration to the open configuration by pushing in the slider 102 in the state of removing the fixing member 64.

As shown in FIG. 17A, when the stopper 72 comes into contact with the step portion 68 of the distal member 67, the distance between the first arm 12 and the second arm 13 of the arm member 11 becomes substantially the maximum value. Subsequently, similarly to the endoscope clip 1 according to the above-described first embodiment, the operator may perform the ligation procedure on the target tissue T using the endoscope clip 2 according to the present embodiment.

(Effect of the Endoscope Clip 2)

In the endoscope clip 2 according to the present embodiment, the fixing member 64 may restrict the relative movement range of the slider 102 with respect to the operating portion main body 101 within the slit 101b of the operating portion main body 101. Accordingly, in the endoscope clip 2 according to the present embodiment, the fixing member 64 may restrict the transition of the arm member 11 from the closed configuration to the open configuration. As a result, similar to the first embodiment, according to the endoscope clip 2 of the present embodiment, when the target tissue T in the body is treated, the closed configuration of the arm member 11 may be easily maintained, and the unintentionally contact of the arm member 11 to the inner wall of the channel of the endoscope and the tissues in the body may be prevented. Since the operation for the operator to adjust the endoscope clip 2 can be shortened, the maneuverability, the operation time, and the efficiency may be improved. Since the fixing member 64 has a simple configuration and is easy to manufacture, the endoscope clip 2 may be configured at low cost.

(First Modification)

Next, an endoscope clip 2A according to a first modification of the present embodiment will be described with reference to FIGS. 18A to 18B. Hereinafter, the description of the same configuration as the endoscope clip 2 according to the second embodiment described above will be omitted, and the difference from the second embodiment will be mainly described.

Figure 18A:
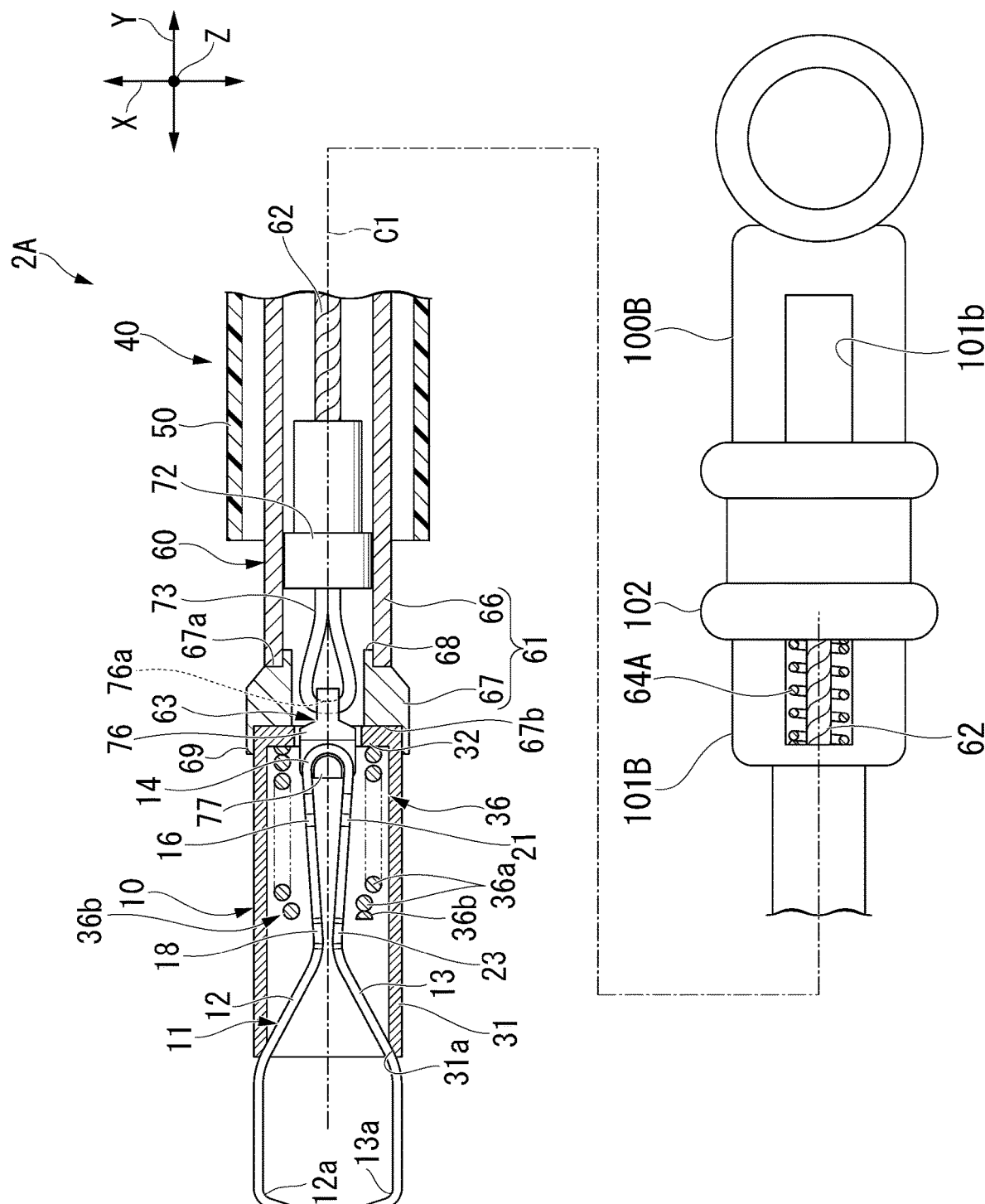
FIG. 18A is a partial cross-sectional side view schematically showing a configuration of an endoscope clip according to a first modification example of the present embodiment.

FIG. 18A is a partial cross-sectional side view schematically showing the configuration of the endoscope clip 2A according to the present modification. More specifically, FIG. 18A is a partial cross-sectional side view showing a state in which the movement of the operation wire 62 toward the distal end side is restricted by the fixing member in the endoscope clip 2A according to the present modification. FIG. 18B is a diagram showing an operation of the endoscope clip 2A according to the present modification.

The endoscope clip 2A according to the present modification is different from the endoscope clip 2 according to the above-described second embodiment in the configuration of the operation unit 100B. As shown in FIG. 18A, in the operation portion 100B of the endoscope clip 2A according to the present modification, the fixing member 64 of the second embodiment is replaced by providing a fixing member 64A.

As shown in FIG. 18A, in the operation portion 100B of the endoscope clip 2A according to the present modification, a fixing member (elastic member, spring) 64A which connects the distal end surface of the slit 101b of the operation portion main body 101B and the distal surface of the slider 102 is provided. The method of connecting the fixing member 64A to the distal surface of the slit 101b of the operation portion main body 101B and the distal surface of the slider 102 is not particularly limited, and various known methods can be used.

For example, the fixing member 64A of the endoscope clip 2A according to the present modification may have a free length similar to the length of the fixing member 64 according to the second embodiment, in the natural state where no external force acts. In present modification, when the operator does not operate the slider 102, the slider 102 is at the same position as the position where the slider 102 contacts the fixing member 64 according to the second embodiment.

In the above description, it is described that the fixing member 64A of the endoscope clip 2A according to the present modification has the free length equivalent to the length of the fixing member 64 according to the second embodiment in the natural state where no external force acts. Actually, the elastic force of the elastic member 36 provided in the pressing tube 31 applies to the arm member 11 and biases the stopper 72 toward the distal end side such that the fixing member 64A is compressed along the direction of the axis C1. However, according to the present modification, the fixing member 64A is configured to have an elastic force larger than the elastic force of the elastic member 36. That is, in the natural state in which no external force applies, the amount of compression of the fixing member 64A only by the elastic force of the elastic member 36 is almost zero. Accordingly, in this state, the fixing member 64A is considered to have the free length equivalent to the length of the fixing member 64 of the endoscope clip 2 according to the second embodiment.

As shown in FIG. 18A, in the endoscope clip 2A according to the present modification, the configuration of the clip 10 and the connection configuration of the clip 10 and the operation wire 62 are similar to the first embodiment. In the endoscope clip 2A according to the present embodiment, the insertion portion 60 includes the sheath 61, the operation wire 62, the connection member 63, and the loop portion 73. Different from the endoscope clip 1 according to the first embodiment, the fixing member 64 is not disposed in the sheath 61.

The endoscope clip 2A according to the present modification has the above-described configuration such that in the natural state where no external force applies, both of a force F1 that is generated by the elastic force of the elastic member 36 for moving the slider 102 toward the distal end side and a force that is generated by the elastic force of the fixing member 64A for pushing back the slider 102 toward the proximal end side apply to the slider 102. As a result, in the endoscope clip 2A according to the present modification, the distance between the distal end surface of the slider 102 and the distal end surface of the slit 101b of the operation portion main body 101B is substantially equal to the free length of the fixing member 64A, and the state of being connected by the fixing member 64A is maintained. According to the present modification, the fixing member 64A can be considered to be a restriction portion configured to restrict the movement of the operation wire 62 toward the distal end side.

In this state, the operation wire 62 connected to the slider 102 and the arm member 11 connected to the operation wire 62 are not possible to advance toward the operation portion main body 101B. As a result, as shown in FIG. 18A, the transition of the arm member 11 from the closed configuration to the open configuration is restricted, and the closed configuration of the arm member 11 is maintained. Accordingly, the fixing member 64A of the endoscope clip 2A according to the present modification may restrict the transition of the arm member 11 from the closed configuration to the open configuration.

The operator presses the slider 102 with a force equal to or larger than the elastic force of the fixing member 64A such that the fixing member 64A is compressed along the direction of the axis C1. At the same time, the operation wire 62 connected to the slider 102 and the arm member 11 connected to the operation wire 62 may advance with respect to the operation portion main body 101B. As shown in FIG. 18B, by the operator pushing the slider 102, the operation wire 62 may be moved to the distal end side until the stopper 72 comes into contact with the step portion 68 of the distal member 67.

In the endoscope clip 2A according to the present embodiment, as the operation wire 62 moves toward the distal end side, in the arm member 11 of the clip 10, part of the first arm 12 and the second arm 13 is in contact with the tapered surface 31a of the pressing tube 31, and the distal ends of the first arm and the second arm 13 are in the separated state. As the operator pushes in the slider 102, the first arm 12 and the second arm 13 of the arm member 11 are separated from each other such that the distance between the distal ends of the first arm 12 and the second arm 13 becomes large. That is, the operator may cause the arm member 11 to be transitioned from the closed configuration to the open configuration by pushing in the slider 102 in the state of compressing the fixing member 64A along the axial direction C1.

Figure 18B:
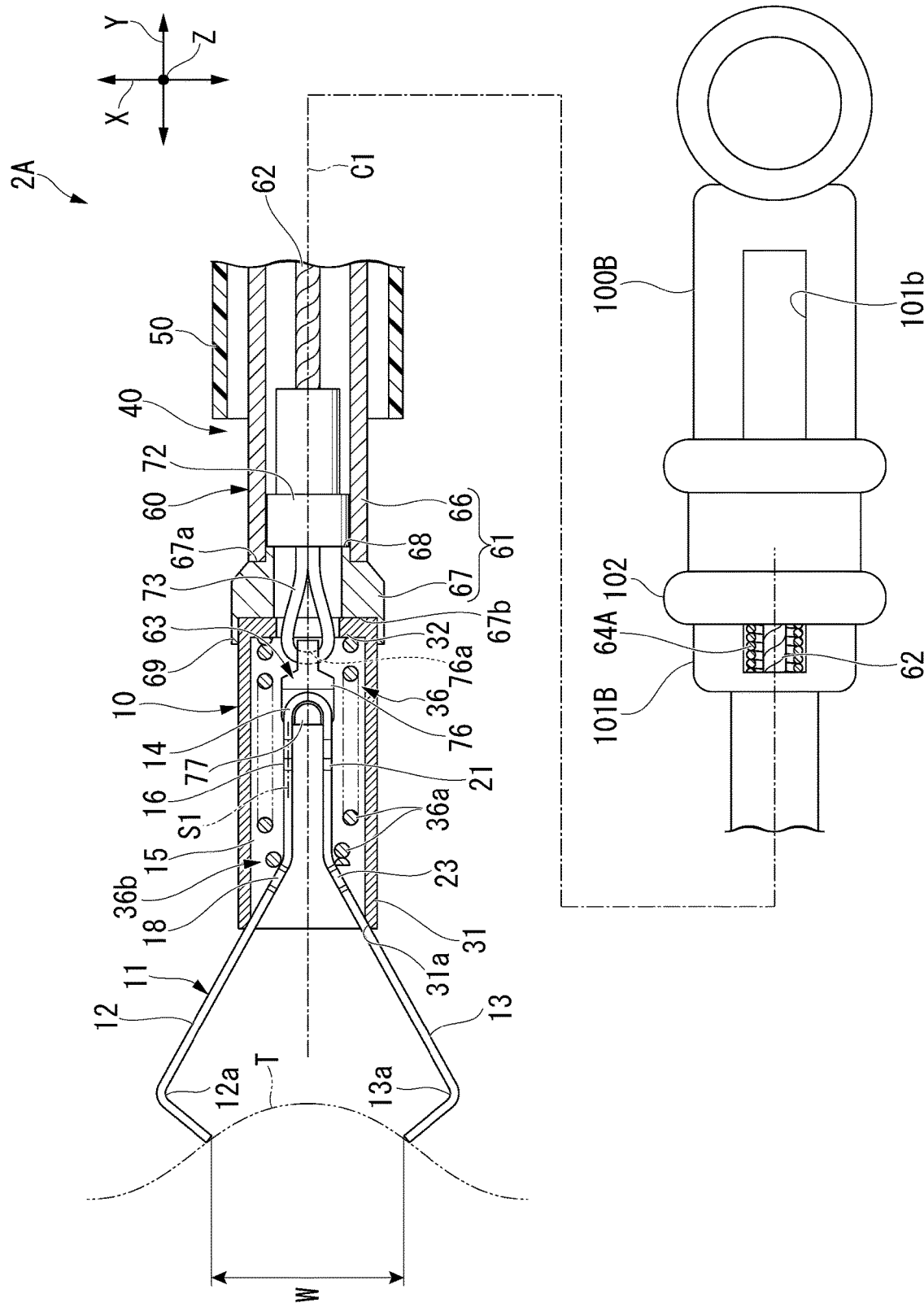
FIG. 18B is a partial cross-sectional side view showing a state of releasing the restriction by a restriction portion of the endoscope clip according to the present modification example.

As shown in FIG. 18B, when the stopper 72 comes into contact with the step portion 68 of the distal member 67, the distance between the first arm 12 and the second arm 13 of the arm member 11 becomes substantially the maximum value. Subsequently, similarly to the endoscope clip 1 according to the above-described first embodiment, the operator may perform the ligation procedure on the target tissue T using the endoscope clip 2A according to the present modification.

(Second Modification)

Next, an endoscope clip 2B according to a second modification of the present embodiment will be described with reference to FIGS. 19A to 19C. Hereinafter, the description of the same configuration as the endoscope clip 2 according to the second embodiment described above will be omitted, and the difference from the second embodiment will be mainly described.

Figure 19B:
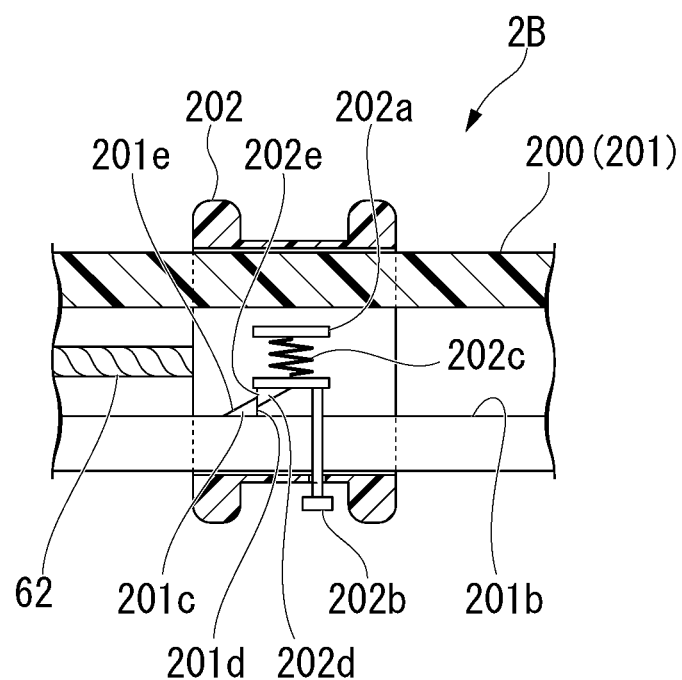
FIG. 19B is a cross-sectional planar view showing a restriction portion in an operation portion of the endoscope clip in FIG. 19A.

FIG. 19A is a partial cross-sectional side view schematically showing the configuration of the endoscope clip 2B according to the present modification. More specifically, FIG. 19A is a partial cross-sectional side view showing a state in which the movement of the operation wire 62 toward the distal end side is restricted by the fixing member in the endoscope clip 2B according to the present modification. FIG. 19B is a diagram showing an operation of the endoscope clip 2A according to the present modification. FIG. 19C is a diagram showing an operation of the endoscope clip 2B according to the present modification.

The endoscope clip 2B according to the present modification is different from the endoscope clip 2 according to the second embodiment in the configuration of the operation unit 100B. More specifically, the endoscope clip 2 according to the second embodiment described above has a configuration in which the slider 102 and the fixing member 64 contact each other to restrict the forward movement of the slider 102 and the operation wire 62. The endoscope clip 2B according to the present modification has a configuration in which the advancement of the slider 102 and the operation wire 62 with respect to the operation portion main body 201 is restricted by the ratchet mechanism.

Specifically, as shown in FIGS. 19A and 19B, in the endoscope clip 2B according to the present modification, a protrusion (first protrusion) 201c is provided on an inner wall of a slit 201b of the operation portion main body 201, and a ratchet mechanism 202a is provided in the slider 202. The ratchet mechanism 202a of the slider 202 has a button 202b, a spring 202c, and a protrusion (second protrusion) 202d.

According to the present modification, as shown in FIG. 19B, the first protrusion 201c has a right triangle shape in a cross section by a plane passing through the central axis of the slit 201b. The first protrusion 201c has a wall portion 201d formed to be orthogonal to the inner wall of the slit 201b and an inclined portion 201e formed in a slope shape. The inclined portion 201e is sequentially separated from the inner wall of the slit 201b toward the proximal end of the operation portion main body 201. A connecting portion between the wall portion 201d and the inclined portion 201e is located in the first protrusion 201c at the largest distance from the inner circumferential surface of the slit 201b. The distance from the inner circumferential surface of the slit 201b as the connecting portion between the wall portion 201d and the inclined portion 201e is defined as a height of the first protrusion 201c. The distance between the wall portion 201d and the distal surface of the slit 201b is equal to the length in the longitudinal axis direction of the fixing member 64 of the endoscope clip 2 according to the second embodiment of the present disclosure.

The second protrusion 202d of the ratchet mechanism 202a has a wall portion 202e formed to be parallel to the wall portion 201d of the first protrusion 201c and an inclined portion 202f formed in a slope shape. According to the present modification, in the natural state where no external force applies, the elastic force of the elastic member 36 disposes in the pressing tube 31 biases the ratchet mechanism 202a disposed in the slider 202 toward the distal end side. Since the spring 202c of the ratchet mechanism 202a biases the second protrusion 202d in the radial direction, the wall portion 201d disposed in the slit 201b and the wall portion 202e disposed in the ratchet mechanism 202a engage with each other.

According to the present modification, the engagement force with which the wall portion 201d disposed in the slit 201b and the wall portion 202e disposed in the ratchet mechanism 202a contact and engage with each other is set to be larger than the elastic force of the elastic member 36. That is, according to the present modification, the engagement between the wall portion 201d and the wall portion 202e is not canceled only by the elastic force of the elastic member 36. According to the present modification, the engagement between the wall portion 201d and the wall portion 202e is not canceled only by the operation of the operator pushing the slider 202 toward the distal side along the direction of the axis C1.

In this state, even if the operator pushes the slider 202 toward the distal side along the axis C1 direction, the slider 202 is not advanceable due to the engagement between the wall portion 201d and the wall portion 202e. That is, the wall portion 201d and the wall portion 202e contact each other, and the first protrusion 201c and the second protrusion 202d engage with each other such that the advancement of the slider 202 along the central axis of the operation portion main body 201 is restricted, and the advancement of the operation wire 62 connected to the slider 202 is restricted.

According to the present modification, for example, the wall portion 201d disposed in the slit 201b may be arranged at a position satisfying that a distance between the distal end surface of the slider 202 and the distal surface of the slit 201b when the first protrusion 201c and the second protrusion 202d are engaged with each other is equal to the length of the fixing member 64 according to the second embodiment in the longitudinal axis direction. The endoscope clip 2B according to the present modification has the above-described configuration such that as shown in FIG. 19A, when the first protrusion 201c of the slit 201b and the second protrusion 202d of the slider 202 are engaged with each other, it is possible to restrict the movement of the slider 202 and the operation wire 62 connected to the slider 202 toward the distal end side. The combination of the ratchet mechanism 202a and the first protrusion 202c provided on the inner wall of the slit 201b of the operation portion main body 201 according to the present modification may be considered to be a restriction portion configured to restrict the movement of the operation wire 62 toward the distal end side.

As shown in FIG. 19A, when the first protrusion 201c of the slit 201b and the second protrusion 202d of the slider 202 are engaged with each other, the arm member 11 is in the closed configuration. That is, the arm member 11 is in a state where the first arm 12 and the second arm 13 are in contact with each other, or in a state where the distance between the distal of the first arm 12 and the distal of the second arm 13 is substantially zero. Part of the first arm 12 and the second arm 13 of the arm member 11 is in contact with the tapered surface 31a of the pressing tube 31.

At this time, the operation wire 62 connected to the slider 102 and the arm member 11 connected to the operation wire 62 are also in a state in which they cannot be advanced with respect to the operation portion main body 201. As a result, as shown in FIG. 19A, the transition of the arm member 11 from the closed configuration to the open configuration is restricted, and the closed configuration of the arm member 11 is maintained. Accordingly, the first projection 202c provided on the inner wall of the ratchet mechanism 202a and the slit 201b of the endoscope clip 2B according to the present modification may restrict the transition of the arm member 11 from the closed configuration to the open configuration.

When the operator pushes the button 202b of the ratchet mechanism 202a in a state where the first protrusion 201c of the slit 201b and the second protrusion 202d of the slider 202 are engaged with each other, the second protrusion 202d of the ratchet mechanism 202a is moved in the radial direction of the operation portion main body 201 (the direction intersecting the longitudinal axis direction of the operation portion). As a result, the second protrusion 202d of the slider 202 climbs on and overcomes the first protrusion 201c of the slit 201b, and the engagement between the first protrusion 201c and the second protrusion 202d is released.

In this state, the restriction to the movement of the slider 202 to the distal side by the ratchet mechanism 202a is released. By pushing the slider 202 by the operator, the slider 202 and the operation wire 62 connected to the slider 202 may move toward the distal end side. At the same time, the arm member 11 connected to the operation wire 62 may advance. As shown in FIG. 19C, when the operator pushes the slider 202, the operation wire 62 may move to the distal end side until the stopper 72 abuts on the step portion 68 of the distal end member 67.

In the endoscope clip 2B according to the present embodiment, as the operation wire 62 moves toward the distal end side, in the arm member 11 of the clip 10, part of the first arm 12 and the second arm 13 is in contact with the tapered surface 31a of the pressing tube 31, and the distal ends of the first arm and the second arm 13 are in the separated state. As the operator pushes in the slider 102, the first arm 12 and the second arm 13 of the arm member 11 are separated from each other such that the distance between the distal ends of the first arm 12 and the second arm 13 becomes large. That is, the operator may cause the arm member 11 to be transitioned from the closed configuration to the open configuration by pushing the slider 202 in the state in which the restriction to the movement of the operation wire 62 toward the distal end side is released by the ratchet mechanism 202a.

As shown in FIG. 19C, when the stopper 72 comes into contact with the step portion 68 of the distal member 67, the distance between the first arm 12 and the second arm 13 of the arm member 11 becomes substantially the maximum value. Subsequently, similarly to the endoscope clip 1 according to the above-described first embodiment, the operator may perform the ligation procedure on the target tissue T using the endoscope clip 2B according to the present modification.

In the present modification, the operator pulls the slider 202 toward the proximal end side in a state where the slider 202 overcomes the first protrusion 201c of the slit 201b such that the inclined portion 202f of the second protrusion 202d may contact the inclined surface of the first protrusion 201c while being movable toward the proximal end side. As a result, the operator may cause the arm member 11 to be transitioned from the open configuration to the closed configuration by pulling back the slider 202 to the proximal end side.

In the endoscope clip 2B according to this modification, an example in which the first protrusion 201c of the slit 201b and the second protrusion 202d of the slider 202 have a cross section of a right triangle has been described, but the configuration of the endoscope clip 2B is not limited thereto. The endoscope clip 2B according to the present modification only has to be configured that the slider 202 is not relatively advanceable with respect to the operation portion main body 201 due to the engagement between the operation portion main body 201 and the slider 202. The specific embodiment of the engagement between the operation portion main body 201 and the slider 202 is not particularly limited.

Other configurations of the endoscope clip 2A according to the first modification and the endoscope clip 2B according to the second modification of the present embodiment are the same with the configurations of the endoscope clip 2 according to the present embodiment. Accordingly, the clip may be indwelled in the target tissue T by the same procedure as described in the present embodiment.

According to the endoscope clip 2 according to the second embodiment of the present disclosure, the endoscope clip 2A according to the first modification, and the endoscope clip 2B according to the second modification, the same effect as the endoscope clip 1 according to the first embodiment may be achieved.

(Procedures by Using Endoscopic Clip 1)

Hereinafter, with reference to FIG. 20 to FIG. 22, the effect according to the endoscope clip 1 according to the first embodiment of the present disclosure will be described again by mainly by focusing on the comparison between the procedures with the endoscope clip 1 according to the first embodiment of the present disclosure and the procedures with the conventional endoscopic treatment tool. In the following description, the endoscope clip 1 according to the above-described embodiment will be described as an example; however, the same procedures may be performed using the endoscope clip 1A according to the modification of the first embodiment, the endoscope clip 2 according to the second embodiment, and the endoscope clips 2A, 2B according to the modification of the second embodiment.

Figure 20:
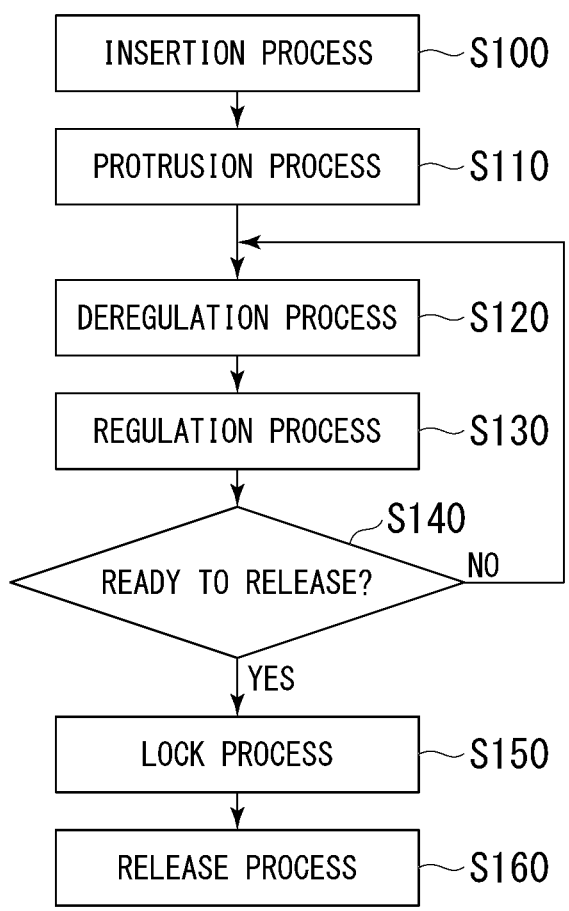
FIG. 20 is a flow-chart showing medical procedures by the endoscope clip according to the present embodiment.

FIG. 20 is a flow chart showing the procedure of the procedure using the endoscope clip 1 according to the first embodiment of the present invention. FIG. 21 is a view showing an example of a configuration of the endoscope treatment tool according to a prior art. FIG. 22 is a flow chart showing the procedure using the conventional endoscopic treatment tool shown in FIG. 21.

As shown in FIG. 20, the procedure for ligating the target tissue T in the body using the endoscope clip 1 according to the first embodiment of the present disclosure includes an insertion step (step S100), a protruding step (step S110), a restriction release step (step S120), a restriction step (target tissue grasping step, step S130), a step of determining whether to release the clip 10 (step S140), a locking step (step S150), and a release step (step S160).

(Step S100) In the insertion step, as shown in FIG. 1A and FIG. 1B, the operator inserts the insertion portion 60 of the endoscope clip 1 into a channel of an endoscope (not shown), and protrudes the insertion portion 60 of the endoscope clip 1 from a distal end opening of the channel. At this time, as shown in FIG. 2, the stopper 72 of the restriction portion 75 is located at the proximal end side more than the fixing member 74 and engaged with each other. The movement of the operation wire 62 toward the distal end side is restricted by the stopper 72 engaging with the fixing member 74. The arm member 11 in the closed configuration is located inside the outer sheath 50.

Subsequently, it proceeds to the protruding step (step S110).

(Step S110) In the protruding step, as shown in FIG. 3, the operator pulls the outer sheath operating portion 51 back to the proximal end side so as to protrude the arm member 11 from the distal end opening of the outer sheath 50. At this time, the engagement state between the stopper 72 of the restriction portion 75 and the fixing member 74 is maintained. The arm member 11 is protruded from the distal opening of the outer sheath 50; however, the closed configuration in which the first arm 12 and the second arm 13 are closed is maintained.

Subsequently, it proceeds to the restriction release step (step S120).

(Step S120) In the restriction releasing step, as shown in FIG. 4, the deforming portion 74b of the fixing member 74 is elastically deformed by the operator pushing the slider 102. At this time, the stopper 72 is moved toward the distal end side with respect to the fixing member 74 and about to climb on and overcome the fixing member 74 in the state in which the engagement state between the stopper 72 of the restriction portion 75 and the fixing member 74 is maintained. Accordingly, the restriction to the movement of the operation wire 62 toward the distal end side by the restriction portion 75 is released. As a result, the arm member 11 may be transitioned from the closed configuration to the open configuration. That is, the first arm 12 and the second arm 13 of the arm member 11 are spaced apart from each other.

As shown in FIG. 6, when the stopper 72 climbs on and overcomes the fixing member 74 to be positioned at the distal end side more than the fixing member 74, the first arm 12 and the second arm 13 of the arm member 11 are separated to be from each other. When the operator pushes the slider 102, the arm member 11 is moved to the distal end side together with the operation wire 62. As shown in FIG. 8 and FIG. 9, when the stopper 72 advances until the stopper 72 comes into contact with the step portion 68 of the distal member 67, the arm member 11 is in the open configuration in which the distance between the first arm 12 and the second arm 13 is substantially the maximum value W1. Subsequently, the operator may grasp the target tissue T by using the arm member 11 in the open configuration.

Then, it proceeds to the restriction process (step S130).

(Step S130) In the restriction step, the operator grasps the target tissue T by using the arm member 11 of the clip 10 in the open configuration. Subsequently, as shown in FIG. 10, the operator may pull the slider 102 back toward the proximal end side to cause the arm member 11 to be transitioned from the open configuration to the closed configuration again and cause the stopper 72 to be positioned at the proximal end side more than the fixing member 74. At this time, the state in which the target tissue T is grasped by the arm member 11 is maintained and the restriction portion 75 may restrict the movement of the operation wire toward the distal end side again.

Subsequently, the operator determines whether or not to indwell the clip 10 in the state in which the target tissue T is grasped by the arm member 11 in the body (step S140).

In the above description, it is described that in order to grasp the target tissue T in step S130, the arm member 11 is transitioned from the open configuration to the closed configuration; however, in order to operate the arm member 11, the arm member 11 may be transitioned from the open configuration to the closed configuration. In this case, the arm member 11 does not grasp the target tissue T.

(Step S140) The operator confirms the state in which the target tissue T is grasped by the arm member 11 using an endoscope (not shown), and determines whether or not to indwell the clip 10 in the body. When the operator determines that the target tissue T is grasped by the arm member 11 in a desired state, the operator proceeds to the locking step (step 150). For example, if the operator determines that the target tissue T is grasped in an undesired state by the arm member 11 or that a different target tissue T is mistakenly grasped, the operator returns to the restriction release step (step S120) and grasp the target tissue T again following the above-described procedures.

(Step S150) When the operator determines that the target tissue T is grasped by the arm member 11 in a desired state, the operator proceeds to the locking step. In the locking process, the operator further pulls the slider 102 back to the proximal end side. At this time, the operation wire 62, the connection member 63, and the arm member 11 are moved to the proximal end side while the target tissue T is grasped by the arm member 11. When the operator pulls the slider 102 back toward the proximal end side, the first engaged portions 16, 17 and the second engaged portions 21, 22 of the arm member 11 are engaged with the engaging portion 32 of the pressing tube 31. In this state, as shown in FIGS. 11A and 11B, the stopper 72 is located at the proximal end side more than the fixing member 74 and separated from the fixing member 74, and the arm member 11 is in the closed configuration.

Accordingly, the positional relationship between the arm member 11 and the pressing tube 31 in the clip 10 is fixed (locked), and even if the operator pushes the slider 102, it is impossible to cause the arm member 11 to be transitioned from the closed configuration to the open configuration.

Subsequently, it processed to the release step (step S160).

(Step S160) In the release step, the operator pushes the slider 120 to move the operation wire 62, the connection member 63, and the clip 10 together toward the distal end side. As shown in FIG. 12, when the connection member 63 is moved to the distal end side more than the distal end member 67 of the sheath 61, the operator may release the clip 10 from the connection member 63 and indwell the clip 10 in the body.

Subsequently, the operator takes necessary measures and ends the series of procedures.

According to the procedure using the endoscope clip 1 according to the above-described first embodiment of the present disclosure, there is no necessity for the operator to operate (grasp) the slider 102 in the protruding step (step S110), the restriction release step (S120), and the restriction step (S130), and the movement of the operation wire 62 toward the distal end side is restricted by the engagement of the stopper 72 and the fixing member 74. Accordingly, according to the procedures using the endoscope clip 1 according to the first embodiment of the present disclosure, the operations of the operator for adjusting the endoscope clip 1 may be shortened such that the maneuverability, the operation time, and the efficiency may be improved.

With regard to the procedures for ligating the target tissue T using the endoscope clip according to each of the other embodiments and modifications of the present disclosure, although the specific operation in the restriction release step (S120) and the restriction step (S130) are different, the same effect as the procedures using the endoscope clip 1 according to the first embodiment described above is achieved.

For example, according to the procedures using the endoscope clip 2 according to the second embodiment of the present disclosure shown in FIGS. 16A to 17B, the operator removes the fixing member 64 from the operation portion 100A in the restriction release step (step S120). Subsequently, in the restriction step (step S130), the operator may reattaches the fixing member 64 to the operation portion 100A, or the operator may continue grasping the slider 102 while the fixing member 64 being removed from the operation portion 100A so as to restrict the transition of the arm member 11 from the closed configuration to the open configuration.

In a case in which the fixing member 64 is not reattached to the operation unit 100A after removing the fixing member 64 from the operation unit 100A in the restriction release step (S120), it is possible to omit the operation of removing the fixing member 64 from the operation portion 100A at the time of performing the restriction release step (Step S120) after the step of determining whether to release the clip 10 (Step S140). Accordingly, for example, when the procedures of the restriction release step (step S120), the restriction step (step S130), and the step of determining whether to release the clip 10 (step S140) is repeated (when the arm member 11 is repeatedly opened and closed), the operation may be performed smoothly.

(Procedures Using Conventional Endoscopic Treatment Tool)

Figure 21:
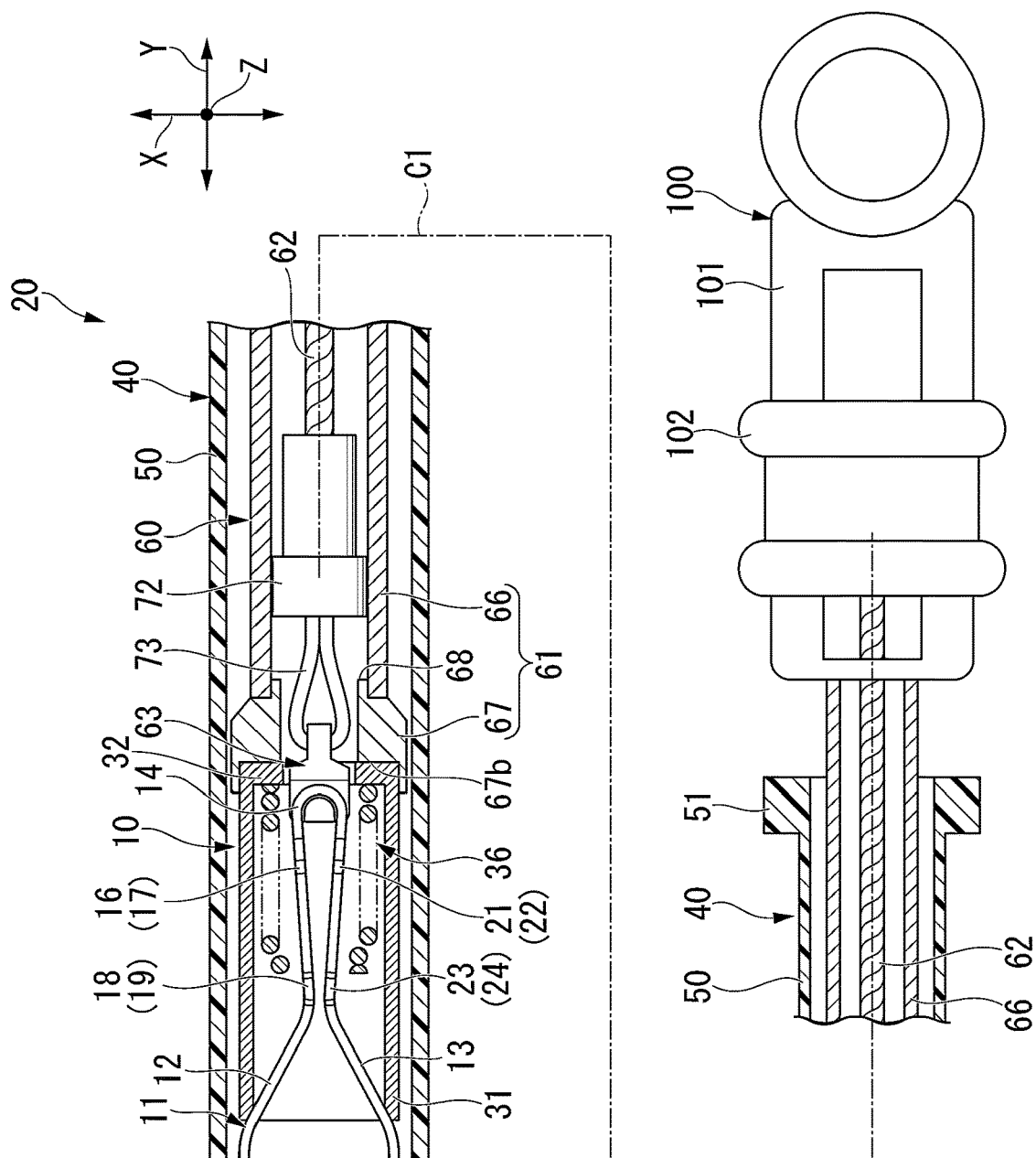
FIG. 21 is a partial cross-sectional view showing a configuration of an endoscope treatment tool according to a prior art.

FIG. 21 is a view showing a configuration of a conventional endoscopic treatment tool 20. As shown in FIG. 21, the conventional endoscopic treatment tool 20 does not include the restriction portion 75 of the endoscope clip 1 according to the present disclosure.

FIG. 22 shows a sequence of procedures using the endoscopic treatment tool 20 according to the prior art. As shown in FIG. 22, the procedures using the endoscopic treatment tool 20 of the prior art includes an inserting step (step S200), a protruding step (step S210), an open-leg step (step S220), a holding step (Step S230), a step of determining whether or not to release the clip 10 (step S240), a locking step (step S250), and a release step (step S260).

(Step S200) In the insertion step, the operator inserts the insertion portion 60 of the endoscopic treatment tool 20 into a channel of an endoscope (not shown), and causes the insertion portion 60 to protrude from the distal end opening of the channel. At this time, the arm member 11 in the closed configuration is located inside the outer sheath 50.

Then, it proceeds to the protruding step (step S210).

(Step S210) In the protruding step, the operator pulls the outer sheath operating portion 51 back toward the proximal end side so as to cause the arm member 11 in the closed configuration to be protruded from the distal end opening of the outer sheath 50. In the endoscope treatment tool 20 of the prior art, since the operation wire 62 does not have a configuration for restricting the movement toward the distal end side, the slider 102 and the operation wire 62 are biased toward the distal end side due to the elastic force of the elastic member 36 disposed in the pressing tube 31. As a result, the arm member 11 may automatically be transitioned from the closed configuration to the open configuration.

In order to prevent such state, in the protruding step, the operator continues to maintain the state in which the slider 102 is pulled toward the proximal end side, and pulls the outer sheath operating portion 51 back toward the proximal end side. As a result, the arm member is protruded from the outer sheath 50 while maintaining the closed configuration.

Subsequently, it proceeds to the open-leg step (step S220).

(Step S220) In the open-leg step, when the operator releases the slider 102, the arm member 11 moves toward the distal side while the first arm 12 and the second arm 13 are spaced apart from each other. When the operator confirms that the arm member 11 is in the open configuration, the operator operates the endoscope to position the target tissue T between the first arm 12 and the second arm 13 of the arm member 11 in the open configuration, and pushes the arm member 11 toward the target tissue T to grasp the target tissue T.

Then, it proceeds to the holding step (step S230).

(Step S230) In the holding step, the operator moves the arm member 11 grasping the target tissue T to the proximal end side by pulling back the slider 102 to the proximal end side. At this time, the first arm 12 and the second arm 13 of the arm member 11 are closed while contacting the tapered surface 31a on the distal end side of the pressing tube 31. That is, the target tissue T is clamped by the arm member 11 that is transitioned from the open configuration to the closed configuration.

However, in the holding step, the operator has to continue pulling the slider 102 in order to prevent the arm member 11 from being transitioned to the open configuration again due to the elastic restoring force of the first arm 12 and the second arm 13 described above. In other words, the operator has to continue pulling the slider 102 until the locking step (step S250) described below is finished.

Subsequently, the operator determines whether or not to indwell the clip 10 grasping the target tissue T by the arm member 11 in the body (step S240).

(Step S240) The operator confirms the state in which the target tissue T is grasped by the arm member 11 using an endoscope (not shown), and determines whether or not the clip 10 is to be indwelled in the body. When the operator determines that the target tissue T is grasped by the arm member 11 in a desired state, the operator proceeds to the locking step (step 250). On the other hand, for example, when the operator determines that the target tissue T is grasped by the arm member 11 in an undesired state, or a different target tissue T is mistakenly grasped, the operator returns to the open-leg step (step S220) to grasp the target tissue T again following the above-described procedures.

As described above, in this step, the operator has to keep the slider 102 being pulled.

(Step S250) When the operator determines that the target tissue T is grasped by the arm member 11 in the desired state, the operator proceeds to the locking step. In the locking step, the operator further pulls the slider 102 back to the proximal end side. At this time, the operation wire 62, the connection member 63, and the arm member 11 are moved to the proximal end side while the target tissue T is grasped by the arm member 11. When the operator pulls the slider 102 back toward the proximal end side, the first engaged portions 16, 17 and the second engaged portions 21, 22 of the arm member 11 are engaged to the engaging portion 32 of the pressing tube 31. In this state, the arm member 11 is in the closed configuration.

As a result, the positional relationship between the arm member 11 and the pressing tube 31 in the clip 10 is fixed (locked), and even if the operator releases hands from the slider 102, it is impossible for the arm member 11 to be transitioned from the closed configuration to the open configuration.

Subsequently, it proceeds to the release step (step S260).

(Step S260) In the release step, the operator pushes the slider 120 to move the operation wire 62, the connection member 63, and the clip 10 together to the distal end side. When the connection member 63 is moved to the distal side of the distal end member 67 of the sheath 61, the operator may release the clip 10 from the connection member 63 and indwell the clip 10 in the body.

Subsequently, the operator takes necessary measures and ends the series of procedures.

As described above, since the endoscope treatment tool 20 of the related art does not have a configuration for restricting the movement of the operation wire 62 toward the distal end side, during the period from the protruding step (step S210) until the locking step (step S250) is finished, it is necessary to maintain the state of pulling the slider 102. As a result, the operations for the operator to adjust the endoscopic treatment tool 20 becomes complicated, and the handling becomes difficult.

Several embodiments and modification examples of the present disclosure have been described above; however, the technical scope of the present disclosure is not limited to the embodiment and the application examples. The present disclosure is not limited to the above-described embodiments and is limited only by the accompanying claims.

What is claimed is:

1. A clip apparatus for use with an endoscope, comprising:
a clip unit;
a first restrictor;
a second restrictor; and
an operation wire configured to move toward a distal direction of the clip unit to cause the clip unit to transition from a closed configuration to an open configuration,
wherein when the clip unit is in the closed configuration:
the clip unit is configured to apply a biasing force to the operation wire toward the distal direction, and
the first restrictor is configured to restrict the clip unit from transitioning from the closed configuration to the open configuration, and
the second restrictor is configured to prohibit the clip unit from transitioning from a locked configuration to the open configuration.

2. The clip apparatus according to claim 1, wherein, when the clip unit is in the closed configuration, the first restrictor is configured to apply a first force to the operation wire toward a proximal direction of the clip unit to restrict the clip unit from transitioning from the closed configuration to the open configuration, and the first force is larger than the biasing force.

3. The clip apparatus according to claim 2,
wherein the first restrictor comprises:
an engaging portion connected to the operation wire and configured to move with the operation wire during the transitioning between the closed configuration and the open configuration; and
an engaged portion configured to prevent the operation wire from moving toward the distal direction by engaging with the engaging portion in the closed configuration while the operation wire is connected to the engaging portion.

4. The clip apparatus according to claim 3, wherein, in a transition between the closed configuration and the open configuration,
the engaging portion is configured to pass through the engaged portion while the operation wire is connected to the engaging portion, and the engaged portion is deformed in a radial direction.

5. The clip apparatus according to claim 4, wherein the engaged portion includes a deforming portion, the deforming portion configured to be deformed in the transition.

6. The clip apparatus according to claim 4, further comprising:
a sheath having a distal end opening,
wherein the engaged portion is disposed less than 1 centimeter from the distal end opening.

7. The clip apparatus according to claim 3, wherein the engaging portion is a stopper.

8. The clip apparatus according to claim 3, wherein the engaged portion comprises:
an inner surface; and
a protrusion inwardly protruded from the inner surface to engage with the engaging portion, the protrusion provided distally relative to a proximal end of the first restrictor.

9. The clip apparatus according to claim 3, wherein the engaging portion is released from the engaged portion when the biasing force is equal to or larger than the first force.

10. The clip apparatus according to claim 3, wherein the engaged portion has an inner diameter that is smaller than an outer diameter of the engaging portion.

11. The clip apparatus according to claim 3, wherein the engaged portion comprises:
a first inclined surface oriented toward the distal direction and the first inclined surface inclined relative to a longitudinal direction of the clip unit and a direction orthogonal to the longitudinal direction; and
a second inclined surface oriented toward the proximal direction, the second inclined surface proximally provided relative to the first inclined surface.

12. The clip apparatus according to claim 2, further comprising an outer sheath configured to insert the clip unit,
wherein when the clip unit is inserted into the outer sheath, the clip unit is in the closed configuration, and when a part of the clip unit protrudes from the outer sheath, the clip unit is able to be transitioned between the closed configuration and the open configuration.

13. The clip apparatus according to claim 2, wherein the clip unit comprises an elastic material configured to apply the biasing force.

14. The clip apparatus according to claim 13, wherein the clip unit comprises a clip sheath and at least one arm of a plurality of arms is provided in the clip sheath,
- wherein the elastic material is disposed inside the clip sheath, and the elastic material is configured to bias the at least one arm toward the distal direction by the biasing force.

15. The clip apparatus according to claim 13,
- wherein the first restrictor comprises:
  - an engaging portion connected to the operation wire and configured to move with the operation wire; and
  - an engaged portion configured to restrict the operation wire from moving toward the distal direction by engaging with the engaging portion in the closed configuration, and
- wherein the engaging portion is released from the engaged portion when a sum of an operation force from the operation wire and the biasing force is equal to or larger than the first force,
- the operation force is configured to be applied from the operation wire toward the distal direction along a longitudinal direction of the clip unit, and
- the first force is configured to be applied from the first restrictor to the operation wire toward the proximal direction.

16. The clip apparatus according to claim 2, wherein a direction of biasing force is opposite to a direction of the first force.

17. The clip apparatus according to claim 2, wherein the operation wire is configured to move toward the proximal direction to cause the clip unit to transition from the open configuration to the closed configuration.

18. The clip apparatus according to claim 1, further comprising:
- an operation portion provided proximally relative to the operation wire, and the operation portion configured to move the operation wire to cause the clip unit to transition between the closed configuration to the open configuration.

19. The clip apparatus according to claim 1, wherein the first restrictor is further configured to, when the clip unit is in the closed configuration, restrict the operation wire from moving toward the distal direction of the clip unit while the operation wire is connected to the first restrictor.

20. The clip apparatus according to claim 1, wherein the closed configuration is a fully closed configuration in which one of a plurality of arms is in contact with another of the plurality of arms or a distance between a distal end of the one of the plurality of arms and a distal end of the other of the plurality of arms is substantially zero.

* * * * *